US012630596B2

(12) United States Patent
Sun

(10) Patent No.: US 12,630,596 B2
(45) Date of Patent: May 19, 2026

(54) ENGINEERED LYSIN-HUMAN DEFENSIN PROTEIN

(71) Applicant: University of South Florida, Tampa, FL (US)

(72) Inventor: Xingmin Sun, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 949 days.

(21) Appl. No.: 17/417,587

(22) PCT Filed: Dec. 23, 2019

(86) PCT No.: PCT/US2019/068252
§ 371 (c)(1),
(2) Date: Jun. 23, 2021

(87) PCT Pub. No.: WO2020/142306
PCT Pub. Date: Jul. 9, 2020

(65) Prior Publication Data
US 2022/0112251 A1 Apr. 14, 2022

Related U.S. Application Data

(60) Provisional application No. 62/784,597, filed on Dec. 24, 2018.

(51) Int. Cl.
| | |
|---|---|
| *A61K 38/00* | (2006.01) |
| *A61P 31/04* | (2006.01) |
| *C07K 14/005* | (2006.01) |
| *C07K 14/47* | (2006.01) |

(52) U.S. Cl.
CPC .......... *C07K 14/4723* (2013.01); *A61P 31/04* (2018.01); *C07K 14/005* (2013.01); *A61K 38/00* (2013.01); *C07K 2319/00* (2013.01)

(58) Field of Classification Search
CPC .. C07K 14/4723; C07K 2319/00; A61P 31/04
See application file for complete search history.

(56) References Cited

U.S. PATENT DOCUMENTS

| | | | |
|---|---|---|---|
| 9,205,133 | B2 | 12/2015 | Dawson et al. |
| 2002/0127219 | A1 | 9/2002 | Okkels et al. |
| 2004/0265337 | A1 | 12/2004 | Zsebo et al. |
| 2010/0239682 | A1 | 9/2010 | Andremont et al. |
| 2016/0045578 | A1 | 2/2016 | Gasson et al. |
| 2018/0353575 | A1 | 12/2018 | Fischetti et al. |

FOREIGN PATENT DOCUMENTS

| | | | | |
|---|---|---|---|---|
| CN | 103957931 | A | 9/2011 | |
| CN | 105555309 | A | 4/2014 | |
| DE | 102014213654 | A1 | 7/2014 | |
| EP | 2679677 | A1 * | 1/2014 | .......... A23K 20/195 |
| WO | WO-2009068858 | A1 * | 6/2009 | ............. A61K 38/50 |
| WO | WO-2015109012 | A1 * | 7/2015 | ............. A61P 11/00 |

OTHER PUBLICATIONS

Furci et al. New Role for Human a-Defensin 5 in the Fight against Hypervirulent Clostridium difficle Strains, Infection and Immunity, 2015, pp. 986-995 (Year: 2015).*
Goh_et_al_2007 (Year: 2007).*
Wang et al ("Using a Novel Lysin To Help Control Clostridium difficile Infections" AAC vol. 59 No. 12; published Nov. 2015)(Year: 2015).*
Zucca_et_al_2011 (Year: 2011).*
Peng_et_al_2019 (Year: 2019).*
International Search Report issued for PCT/US2019/068252, mailed Jul. 28, 2020.
Peng et al., A Novel Bacteriophage Lysin-Human Defensin Fusion Protein is Effective in Treatment of Clostridioldes difficile Infection in Mice, Frontiers Microbiol, vol. 9, No. 3234, 1-10, 2019.
Wang, Qiong, et al. "Using a novel lysin to help control Clostridium difficile infections." Antimicrobial agents and chemotherapy 59.12 (2015): 7447-7457.
Furci, Lucinda, et al. "New role for human α-defensin 5 in the fight against hypervirulent Clostridium difficile strains." Infection and immunity 83.3 (2015): 986-995.
Giesemann, Torsten, Gregor Guttenberg, and Klaus Aktories. "Human α-defensins inhibit Clostridium difficile toxin B." Gastroenterology 134.7 (2008): 2049-2058.
Simmons, Mustafa, et al. "Recombinant expression of two bacteriophage proteins that lyse Clostridium perfringens and share identical sequences in the C-terminal cell wall binding domain of the molecules but are dissimilar in their N-terminal active domains." Journal of agricultural and food chemistry 58.19 (2010): 10330-10337.
Peng, Zhong, et al. "Advances in the diagnosis and treatment of Clostridium difficile infections." Emerging microbes & infections 7.1 (2018): 1-13.
Pero, Raffaela, et al. "β-Defensins in the Fight against Helicobacter pylori." Molecules 22.3 (2017): 424.
Hookman, Perry, and Jamie S. Barkin. "Clostridium difficile associated infection, diarrhea and colitis." World journal of gastroenterology: WJG 15.13 (2009): 1554.
Mayer, Melinda J., Michael J. Gasson, and Arjan Narbad. "Genomic sequence of bacteriophage ATCC 8074-B1 and activity of its endolysin and engineered variants against Clostridium sporogenes." Applied and environmental microbiology 78.10 (2012): 3685-3692.
Kudryashova, Elena, et al. "Human defensins facilitate local unfolding of thermodynamically unstable regions of bacterial protein toxins." Immunity 41.5 (2014): 709-721.
Alyousef, Abdullah. Identification and characterisation of lysin enzymes as potential therapeutics for the treatment of Clostridium difficile. Diss. Cardiff University, (2013): 317 pages.

(Continued)

*Primary Examiner* — Catherine S Hibbert
(74) *Attorney, Agent, or Firm* — HUSCH BLACKWELL LLP

(57) ABSTRACT

*Clostridium difficile*, reclassified as *Clostridioides difficile*, is a Gram-positive, spore-forming, anaerobic, and toxin-producing nosocomial pathogen. Since the first description of a *C. difficile*-associated disease (CDAD)-like case in 1892, *C. difficile* infection (CDI) has become a high-impact health care-associated infection throughout the world, especially in the developed countries. Described herein are methods of treating *Clostridium difficile* infection in a subject in need thereof by administering an amount of the engineered lysin-human defensin (LHD) protein(s) described herein.

13 Claims, 14 Drawing Sheets

Specification includes a Sequence Listing.

(56) References Cited

OTHER PUBLICATIONS

Zucca, Mario, Sara Scutera, and Dianella Savoia. "Novel avenues for Clostridium difficile infection drug discovery." Expert opinion on drug discovery 8.4 (2013): 459-477.

Mayer, Melinda J., Arjan Narbad, and Michael J. Gasson. "Molecular characterization of a Clostridium difficile bacteriophage and its cloned biologically active endolysin." Journal of bacteriology 190. 20 (2008): 6734-6740.

Polymedix, "Revolutionizing the Treatment of Infectious Diseases with Defensin-Mimetics", (2012): 37 pages.

Lopez-Urena, D., et al. "Role of Clostridium difficile toxins in antibiotic-associated diarrhea and pseudomembranous colitis." Microb Toxins (2018): 153-170.

* cited by examiner

SEQUENCE LISTING

<160> NUMBER OF SEQ ID NOS: 5

<210> SEQ ID NO 1
<211> LENGTH: 226
<212> TYPE: PRT
<213> ORGANISM: Artificial Sequence
<220> FEATURE:
<223> OTHER INFORMATION: Synthetic Construct

<400> SEQUENCE: 1

Met Lys Ile Cys Ile Thr Val Gly His Ser Ile Leu Lys Ser Gly Ala
1               5                   10                  15

Cys Thr Ser Ala Asp Gly Val Val Asn Glu Tyr Gln Tyr Asn Lys Ser
                20                  25                  30

Leu Ala Pro Val Leu Ala Asp Thr Phe Arg Lys Glu Gly His Lys Val
            35                  40                  45

Asp Val Ile Ile Cys Pro Glu Lys Gln Phe Lys Thr Lys Asn Glu Glu
        50                  55                  60

Lys Ser Tyr Lys Ile Pro Arg Val Asn Ser Gly Gly Tyr Asp Leu Leu
65                  70                  75                  80

Ile Glu Leu His Leu Asn Ala Ser Asn Gly Gln Gly Lys Gly Ser Glu
                85                  90                  95

Val Leu Tyr Tyr Ser Asn Lys Gly Leu Glu Tyr Ala Thr Arg Ile Cys
            100                 105                 110

Asp Lys Leu Gly Thr Val Phe Lys Asn Arg Gly Ala Lys Leu Asp Lys
            115                 120                 125

Arg Leu Tyr Ile Leu Asn Ser Ser Lys Pro Thr Ala Val Leu Ile Glu
            130                 135                 140

Ser Phe Phe Cys Asp Asn Lys Glu Asp Tyr Asp Lys Ala Lys Lys Leu
145                 150                 155                 160

Gly His Glu Gly Ile Ala Lys Leu Ile Val Glu Gly Val Leu Asn Lys
                165                 170                 175

Asn Ile Asn Gly Gly Gly Gly Ser Gly Gly Gly Gly Ser Gly Gly Gly
                180                 185                 190

Gly Ser Ala Thr Cys Tyr Cys Arg Thr Gly Arg Cys Ala Thr Arg Glu
            195                 200                 205

Ser Leu Ser Gly Val Cys Glu Ile Ser Gly Arg Leu Tyr Arg Leu Cys
        210                 215                 220

Cys Arg
225

<210> SEQ ID NO 2
<211> LENGTH: 179
<212> TYPE: PRT
<213> ORGANISM: Artificial Sequence
<220> FEATURE:
<223> OTHER INFORMATION: Synthetic Construct

<400> SEQUENCE: 2

Met Lys Ile Cys Ile Thr Val Gly His Ser Ile Leu Lys Ser Gly Ala
1               5                   10                  15

Cys Thr Ser Ala Asp Gly Val Val Asn Glu Tyr Gln Tyr Asn Lys Ser
                20                  25                  30

Leu Ala Pro Val Leu Ala Asp Thr Phe Arg Lys Glu Gly His Lys Val
            35                  40                  45

Asp Val Ile Ile Cys Pro Glu Lys Gln Phe Lys Thr Lys Asn Glu Glu
        50                  55                  60

```
Lys Ser Tyr Lys Ile Pro Arg Val Asn Ser Gly Gly Tyr Asp Leu Leu
65              70              75              80

Ile Glu Leu His Leu Asn Ala Ser Asn Gly Gln Gly Lys Gly Ser Glu
                85              90              95

Val Leu Tyr Tyr Ser Asn Lys Gly Leu Glu Tyr Ala Thr Arg Ile Cys
            100             105             110

Asp Lys Leu Gly Thr Val Phe Lys Asn Arg Gly Ala Lys Leu Asp Lys
        115             120             125

Arg Leu Tyr Ile Leu Asn Ser Ser Lys Pro Thr Ala Val Leu Ile Glu
    130             135             140

Ser Phe Phe Cys Asp Asn Lys Glu Asp Tyr Asp Lys Ala Lys Lys Leu
145             150             155             160

Gly His Glu Gly Ile Ala Lys Leu Ile Val Glu Gly Val Leu Asn Lys
                165             170             175

Asn Ile Asn

<210> SEQ ID NO 3
<211> LENGTH: 32
<212> TYPE: PRT
<213> ORGANISM: Artificial Sequence
<220> FEATURE:
<223> OTHER INFORMATION: Synthetic Construct

<400> SEQUENCE: 3

Ala Thr Cys Tyr Cys Arg Thr Gly Arg Cys Ala Thr Arg Glu Ser Leu
1               5               10              15

Ser Gly Val Cys Glu Ile Ser Gly Arg Leu Tyr Arg Leu Cys Cys Arg
            20              25              30

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Gly Gly Gly Gly Ser Gly Gly Gly Gly Ser Gly Gly Gly Gly Ser
1               5               10              15

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Gly Gly Gly Gly Ser
1               5
```

ENGINEERED LYSIN-HUMAN DEFENSIN PROTEIN

CROSS-REFERENCE TO RELATED APPLICATIONS

This application is a National Stage of International Application No. PCT/US2019/068252, filed Dec. 23, 2019, which claims benefit of U.S. Provisional Application No. 62/784,597, filed Dec. 24, 2018, which is hereby incorporated herein by reference in its entirety.

STATEMENT REGARDING FEDERALLY SPONSORED RESEARCH OR DEVELOPMENT

This invention was made with Government support AI132711, DK112004, and DK092352 awarded by the National Institutes of Health. The Government has certain rights in the invention.

SEQUENCE LISTING

This application contains a sequence listing filed in electronic form as an ASCII.txt file entitled "292103-2980 Sequence Listing_ST25" created on Dec. 21, 2019. The content of the sequence listing is incorporated herein in its entirety.

BACKGROUND

*Clostridium difficile*, reclassified as *Clostridioides difficile* (Lawson, Citron et al. 2016), is a Gram-positive, spore-forming, anaerobic, and toxin-producing nosocomial pathogen. Since the first description of a *C. difficile*-associated disease (CDAD)-like case in 1892 (Finney 1893), *C. difficile* infection (CDI) has become a high-impact health care-associated infection throughout the world, especially in the developed countries. In the United States, *C. difficile* is listed as one of the three most urgent antibiotic resistance threats by the Centers for Disease Control and Prevention (CDC) (CDC 2013), and CDI is responsible for approximately 453,000 cases of infections and 29,000 deaths every year, with an annual economic burden ranging from $436 million to $3 billion dollars (Napolitano and Edmiston 2017). In Europe, CDI was associated with considerable short or long term disability, 8382 deaths per year (Cassini, Plachouras et al. 2016), and an annual economic burden of €3 billion euro (Reigadas Ramirez and Bouza 2018).

Currently, oral antibiotics such as metronidazole, vancomycin and fidaxomicin is still recommended treatment for CDI (Debast, Bauer et al. 2014, McDonald, Gerding et al. 2018). However, *C. difficile* isolates with significantly reduced susceptibility, and even resistance to these recommended antibiotics have been frequently identified and reported (Spigaglia 2016, Peng, Addisu et al. 2017, Peng, Jin et al. 2017). As such there exists a need for treatments for CDI.

SUMMARY

Described herein are engineered lysin-human defensin (LHD) proteins and pharmaceutical formulations thereof. Also described herein are methods of treating CDI in a subject by administering an engineered LHD protein described herein to the subject.

The details of one or more embodiments of the invention are set forth in the accompanying drawings and the description below. Other features, objects, and advantages of the invention will be apparent from the description and drawings, and from the claims.

DESCRIPTION OF DRAWINGS

Further aspects of the present disclosure will be readily appreciated upon review of the detailed description of its various embodiments, described below, when taken in conjunction with the accompanying drawings.

(FIG. 2A) SDS-PAGE gel analysis of protein LHD induced and expressed in cell pellet (Lane 1) and supernatant (Lane 2) at 15° C., overnight; (FIG. 2B) SDS-PAGE gel analysis of protein LCD induced and expressed in cell pellet (Lane 1) and supernatant (Lane 2) at 37° C. for 3 hr; (FIG. 2C) SDS-PAGE gel analysis of purified LHD and LCD.

(FIG. 5A) LHD inhibits TcdB-induced cell rounding. CT26 cells in 12-well plates were exposed to HD or LHD at 750 ng/ml (50 times of TcdB concentration) or nothing for 1 hour, followed by exposure to TcdB at 15 ng/ml for 5 hours. (FIG. 5B) Western-blot analysis of non-glucosylated Rac1 in CT26 cells treated with TcdB in the presence or absence of LHD or HD. TcdB glucosylates Rac1 in cells, serving as a readout for toxin cytotoxicity. Quantitation of Rac1 levels in Western-blot was shown in low panel (*$p<0.05$). (FIG. 5C) CT26 cells were lysed, and the cytosolic fraction was exposed to TcdB (15 ng/ml) with or without HD at 750 ng/ml (50 times of TcdB concentration) or LHD at 1500 ng/ml (same molecular concentration as HD) or nothing for 1 h followed by Western Blot analysis using a monoclonal antibody that only recognizes non-glucosylated Rac1. β-actin was used as an equal loading control. Quantitation of Rac1 levels in Western-blot was shown in low panel (****$p<0.0001$).

DETAILED DESCRIPTION

Figure 1:
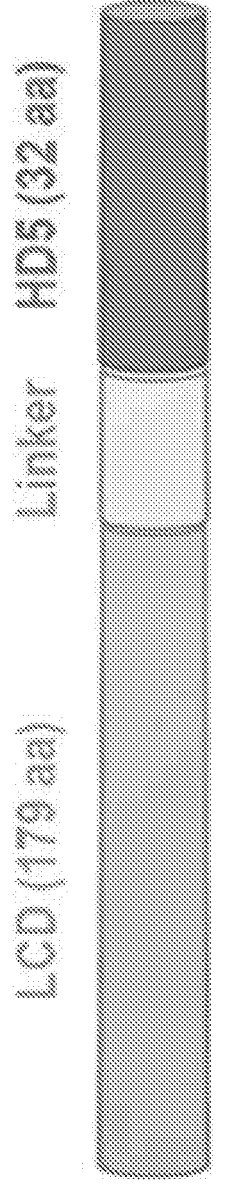
FIG. 1 shows a design of LHD fusion protein as described herein.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, organic chemistry, biochemistry, physiology, cell biology, immunology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "administering" refers to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoans.

The term "biocompatible", as used herein, refers to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, "chemotherapeutic agent" or "chemotherapeutic" can refer to a therapeutic agent utilized to prevent or treat cancer.

As used herein, "control" refers to an alternative subject or sample used in an experiment for comparison purpose and included to minimize or distinguish the effect of variables other than an independent variable.

As used herein with reference to the relationship between DNA, cDNA, cRNA, RNA, protein/peptides, and the like "corresponding to" refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "DNA molecule" can include nucleic acids/polynucleotides that are made of DNA.

As used herein, "dose," "unit dose," or "dosage" refers to physically discrete units suitable for use in a subject, each unit containing a predetermined quantity of a recombinant LHD protein described herein and/or a pharmaceutical formulation thereof calculated to produce the desired response or responses in association with its administration.

As used herein, "effective amount" refers to the amount of a compound provided herein that is sufficient to effect beneficial or desired biological, emotional, medical, or clinical response of a cell, tissue, system, animal, or human.

An effective amount can be administered in one or more administrations, applications, or dosages. The term cam also include within its scope amounts effective to enhance or restore to substantially normal physiological function. The "effective amount" can refer to the amount of a recombinant LHD protein described herein described herein that can kill, lyse, and/or inhibit *Clostridium difficile* and/or inhibit, reduce, and/or eliminate one or more *Clostridium difficile* toxins or effects thereof.

As used herein, the term "encode" refers to principle that DNA can be transcribed into RNA, which can then be translated into amino acid sequences that can form proteins.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins. In some instances, "expression" can also be a reflection of the stability of a given RNA. For example, when one measures RNA, depending on the method of detection and/or quantification of the RNA as well as other techniques used in conjunction with RNA detection and/or quantification, it can be that increased/decreased RNA transcript levels are the result of increased/decreased transcription and/or increased/decreased stability and/or degradation of the RNA transcript. One of ordinary skill in the art will appreciate these techniques and the relation "expression" in these various contexts to the underlying biological mechanisms.

As used herein, "gene" refers to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA.

As used herein, "identity," refers to a relationship between two or more nucleotide or polypeptide sequences, as determined by comparing the sequences. In the art, "identity" can also refers to the degree of sequence relatedness between nucleotide or polypeptide sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. andDevereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

As used herein, "immunomodulator," refers to an agent, such as a therapeutic agent, which is capable of modulating or regulating one or more immune function or response.

As used herein, "mammal," refers to any animal classified as a mammal, including human, domestic and farm animals, nonhuman primates, and zoo, sports, or pet animals, such as, but not limited to, dogs, horses, cats, and cows.

As used herein, "microRNA" refers to a small non-coding RNA molecule containing about 21 to about 23 nucleotides found in organisms, which functions in transcriptional and post-transcriptional regulation of transcription and translation of RNA. "MicroRNA" can exist as part of a larger nucleic acid molecule such as a stem-loop structure that can be processed by a cell and yield a microRNA of about 21-23 nucleotides.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "nucleic acid," "nucleotide sequence," and "polynucleotide" can be used interchangeably herein and generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used herein, "operatively linked" in the context of recombinant DNA molecules, vectors, and the like refers to the regulatory and other sequences useful for expression, stabilization, replication, and the like of the coding and transcribed non-coding sequences of a nucleic acid that are placed in the nucleic acid molecule in the appropriate positions relative to the coding sequence so as to effect expression or other characteristic of the coding sequence or transcribed non-coding sequence. This same term can be applied to the arrangement of coding sequences, non-coding and/or transcription control elements (e.g. promoters, enhancers, and termination elements), and/or selectable markers in an expression vector. "Operatively linked" can also refer to an indirect attachment (i.e. not a direct fusion) of two or more polynucleotides or polypeptides to each other via a linking molecule (also referred to herein as a linker) or the direct fusion of two or more polynucleotides or polypeptides.

As used herein, "overexpressed" or "overexpression" refers to an increased expression level of an RNA and/or protein product encoded by a gene as compared to the level of expression of the RNA or protein product in a normal or control cell. The amount of increased expression as compared to a normal or control cell can be about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.2, 2.4, 2.6, 2.8, 3.0, 3.3, 3.6, 3.9, 4.0, 4.4, 4.8, 5.0, 5.5, 6, 6.5, 7, 7.5, 8.0, 8.5, 9, 9.5, 10, 11, 12, 13, 14, 15, 16, 17, 18, 19, 20, 25, 30, 35, 40, 45, 50, 60, 70, 0, 90, 100 fold or more greater than the normal or control cell.

As used herein, "patient" refers to an organism, host, or subject in need of treatment.

As used herein "peptide" refers to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "plasmid" refers to a non-chromosomal double-stranded DNA sequence including an intact "replicon" such that the plasmid is replicated in a host cell.

As used herein, "positive control" refers to a "control" that is designed to produce the desired result, provided that all reagents are functioning properly and that the experiment is properly conducted.

As used herein, "preventative" and "prevent" refers to hindering or stopping a disease or condition before it occurs, even if undiagnosed, or while the disease or condition is still in the sub-clinical phase.

As used herein, "polypeptides" or "proteins" refers to amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (lie, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). "Protein" and "Polypeptide" can refer to a molecule composed of one or more chains of amino acids in a specific order. The term protein is used interchangeable with "polypeptide." The order is determined by the base sequence of nucleotides in the gene coding for the protein. Proteins can be required for the structure, function, and regulation of the body's cells, tissues, and organs.

As used herein, "promoter" includes all sequences capable of driving transcription of a coding or a non-coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, the term "recombinant" or "engineered" are used interchangeably herein and generally refer to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc. Recombinant or engineered can also refer to the polypeptide encoded by the recombinant nucleic acid. Non-naturally occurring nucleic acids or polypeptides include nucleic acids and polypeptides modified by man.

As used herein, "separated" can refer to the state of being physically divided from the original source or population such that the separated compound, agent, particle, or molecule can no longer be considered part of the original source or population.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, "substantially pure" means an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired result(s). For example, a therapeutically effective amount refers to an amount needed to achieve one or more therapeutic effects.

A "suitable control" is a control that will be instantly appreciated by one of ordinary skill in the art as one that is included such that it can be determined if the variable being evaluated an effect, such as a desired effect or hypothesized effect. One of ordinary skill in the art will also instantly appreciate based on inter alia, the context, the variable(s), the desired or hypothesized effect, what is a suitable or an appropriate control needed.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as *Clostridium difficile* and/or a symptom thereof. The effect can be therapeutic in terms of a partial or complete cure of a disease, condition, symptom or adverse effect attributed to the disease, disorder, or condition. The term "treatment" as used herein covers any treatment of *Clostridium difficile* and/or a symptom thereof, in a subject, particularly a human, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "variant" can refer to a polynucleotide or polypeptide that differs from a reference polynucleotide or polypeptide, but retains essential and/or characteristic properties (structural and/or functional) of the reference polynucleotide or polypeptide (this includes homologues, orthologues, and paralogues, etc.). A typical variant of a polypeptide differs in amino acid sequence from another, reference polypeptide. The differences can be limited so that the sequences of the reference polypeptide and the variant are closely similar overall and, in many regions, identical. A variant and reference polypeptide may differ in nucleic or amino acid sequence by one or more modifications at the sequence level or post-transcriptional or post-translational modifications (e.g., substitutions, additions, deletions, methylation, glycosylations, etc.). A substituted nucleic acid may or may not be an unmodified nucleic acid of adenine, thiamine, guanine, cytosine, uracil, including any chemically, enzymatically or metabolically modified forms of these or other nucleotides. A substituted amino acid residue may or may not be one encoded by the genetic code. A variant of a polypeptide may be naturally occurring such as an allelic variant, or it may be a variant that is not known to occur naturally. "Variant" includes functional and structural variants.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, "wild-type" refers to the typical or average from of a gene, protein, species, organism, etc. as it occurs in a given population.

Discussion

Described herein are engineered lysin-human defensin (LHD) proteins and pharmaceutical formulations thereof. Also described herein are methods of treating CDI in a subject by administering an engineered LHD protein described herein to the subject. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Engineered Lysin-human Defensin (LHD) Proteins

Described herein are engineered LHD proteins. The engineered LHD proteins can specifically lyse *Clostridium difficile* while not lysing beneficial or good bacterial cells. The engineered LHD proteins can be composed of a lysin polypeptide operatively coupled to a human defensin polypeptide. The lysin polypeptide can be directly fused to the human defensin polypeptide. The lysin polypeptide can be indirectly attached to the human defensin polypeptide via a linker. The lysin polypeptide can be operatively coupled to the N-terminus of the human defensin polypeptide. The lysin polypeptide can be operatively coupled to the C-terminus of the human defensin polypeptide. In some embodiments, the engineered LHD protein can be composed of a polypeptide that can be about 65, 70, 75, 80, 85, 90, or 95% to 100% identical to MKICITVGHSILKSGACTSADGVVNE-YQYNKSLAPVLADTFRKEGHKVDVIICPEKQF KTK-NEEKSYKIPRVNSGGYDLLIELHLNASNGQGKG-SEVLYYSNKGLEYATRICDKL GTVFKNRGAKLDKR-LYILNSSKPTAVLIESFFCDNKEDYDKAKKLGHEGIAK-LIVEGV LNKNINGGGGSGGGGSGGGGSATC-YCRTGRCATRESLSGVCEISGRLYRLCCR (SEQ ID NO:1). In some embodiments, the engineered LHD protein can be composed of a polypeptide that can be a homologue or another variant of a polypeptide that can be about 65, 70, 75, 80, 85, 90, or 95% to 100% identical to SEQ ID NO:1.

The lysin polypeptide can be or contain a catalytic domain of a *C. difficile* phage phiC2 lysin (see e.g. NCBI reference sequence NC_009231) or variant thereof. The lysin polypeptide can be about 65, 70, 75, 80, 85, 90, or 95% to 100% identical to MKICITVGHSILKSGACTSADGVVNE-YQYNKSLAPVLADTFRKEGHKVDVIICPEKQF KTK-NEEKSYKIPRVNSGGYDLLIELHLNASNGQGKG-SEVLYYSNKGLEYATRICDKL GTVFKNRGAKLDKR-LYILNSSKPTAVLIESFFCDNKEDYDKAKKLGHEGIAK-LIVEGV LNKNIN (SEQ ID NO:2). In some embodiments, the lysin polypeptide can be a homologue or another variant of a polypeptide that can be about 65, 70, 75, 80, 85, 90, or 95% to 100% identical to SEQ ID NO:2.

The human defensin polypeptide can be a human alpha-defensin polypeptide or a variant thereof. The human defensin polypeptide can be a human alpha-defensin 5 polypeptide or a variant thereof. The human defensin polypeptide can be about 65, 70, 75, 80, 85, 90, or 95% to 100% identical to ATCYCRTGRCATRESLSGVCEISGR-LYRLCCR (SEQ ID NO:3). In some embodiments, the human defensing polypeptide can be homologue or another a variant of a polypeptide that can be about 65, 70, 75, 80, 85, 90, or 95% to 100% identical to SEQ ID NO:3.

The linker can be a peptide linker. In some embodiments, the linker can be GGGGSGGGGSGGGGS (SEQ ID NO:4).

The linker can be composed of one or more repeat units (e.g. 1, 2, 3, 4, 5, 6, 7, 8, 9, 10, etc. repeat units). In some embodiments, the repeat unit of a linker can have a sequence according to GGGGS (SEQ ID NO:5).

It will be appreciated that the recombinant LHD proteins described herein can be generated and obtained by using a suitable prokaryotic or eukaryotic cell system using typical recombinant gene and protein cloning, expression, and purification techniques. Such systems and techniques are generally known in the art. Thus, also described herein are polynucleotides that can encode one or more of the recombinant LHD proteins described herein. Also described herein are vectors that can contain one or more of the polynucleotides that can encode one or more of the recombinant LHD proteins described herein. The vector can be an expression vector and can contain one or more regulator sequences that can be operatively linked to a polypeptide that can encode one or more of the recombinant LHD proteins described herein. Also described herein is a cell or population thereof that contains and/or expresses one or more polypeptides that can encode one or more of the recombinant LHD proteins described herein. The cell can be a prokaryotic cell (e.g. a bacterial or yeast cell). The cell can be a eukaryotic cell (e.g. a Chinese hamster ovary cell, a mouse embryonic fibroblast cell, a mouse myeloma cell etc.). Suitable prokaryotic and eukaryotic cells for protein expression are generally known in the art. Also described herein is a cell or a population thereof that contains one or more recombinant LHD proteins described herein.

Pharmaceutical Formulations Containing an Engineered LHD Protein.

Described herein are pharmaceutical formulations that can contain an amount of an engineered LHD protein described herein. The engineered LHD protein described herein can be provided to a subject in need thereof alone or as an active ingredient, such as in a pharmaceutical formulation. In some embodiments, the pharmaceutical formulations contain a therapeutically effective amount of an engineered LHD protein. The pharmaceutical formulations described herein can be administered to a subject in need thereof. The subject in need thereof can have *Clostridium difficile* or a symptom thereof.

Pharmaceutically Acceptable Carriers and Auxiliary Ingredients and Agents

The pharmaceutical formulations containing a therapeutically effective amount of an engineered LHD protein described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the therapeutically effective amount of an engineered LHD proteins the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, chemotherapeutics and combinations thereof.

Effective Amounts of the Engineered LHD Proteins and Auxiliary Agents

The pharmaceutical formulations can contain a therapeutically effective amount of an engineered LHD protein. In some embodiments the pharmaceutical formulations can also include a therapeutically effective amount of an auxiliary agent. In some embodiments, the therapeutically effective amount of the engineered LHD protein can range from about 1 µg/kg to about 1,000 mg/kg. In further embodiments, the therapeutically effective amount of the engineered LHD protein can range from 1 ng/kg bodyweight to about 0.1 mg/kg bodyweight. The therapeutically effective amount of the engineered LHD protein can range from about 1 pg to about 10 g. In some embodiments, the therapeutically effective amount of the engineered LHD protein can range from about 10 nL to about 10 mL. In some embodiments, the therapeutically effective amount of the engineered LHD protein can ranges from about 10 nL to about 1 µL. For some embodiments, the therapeutically effective amount of the engineered LHD protein can range from about 1 ng to about 1,000 µg per injection, if administered via injection.

In some embodiments, the therapeutically effective amount of the engineered LHD protein can be from about 1 to about 1,000 micrograms per injection, such as for a systemically administered injection. In additional embodiments, the therapeutically effective amount of the engineered LHD protein can range from about 100 to about 5,000 µL per injection, such as for a systemically administered injection.

In embodiments where there is an auxiliary active agent contained in the pharmaceutical formulation in addition to the engineered LHD protein, the therapeutically effective amount of the auxiliary active agent will vary depending on the auxiliary active agent. In some embodiments, the effective amount of the auxiliary active agent ranges from 0.001 micrograms to about 1 milligram. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravitreal, intracerebral, gingival, subgingival, intracerebroventricular, and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of the engineered LHD protein. The oral dosage form can be administered to a subject in need thereof.

Where appropriate, the dosage forms described herein can be microencapsulated. The dosage form can also be prepared to prolong or sustain the release of any ingredient. In some embodiments, the engineered LHD protein can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the engineered LHD protein, auxiliary active ingredient, and/or pharmaceutically acceptable salt thereof can be formulated with a paraffinic or water-miscible ointment base. In some embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the engineered LHD protein, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient (e.g. the engineered LHD proteins or pharmaceutical formulations thereof and/or auxiliary active agent), which may be generated by various types of metered dose pressurized aerosols, nebulizers, or insufflators.

In some embodiments, the dosage forms can be aerosol formulations suitable for administration by inhalation. In some of these embodiments, the aerosol formulation can contain a solution or fine suspension of the engineered LHD protein, auxiliary agent thereof, and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of the engineered LHD protein. In further embodiments, the aerosol formulation can also contain co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulation. In addition to the engineered LHD protein, an auxiliary active ingredient, and/or pharmaceutically acceptable salt thereof, such a dosage form can contain a powder base such as lactose, glucose, trehalose, manitol, and/or starch. In some of these embodiments, the engineered LHD protein, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol dosage forms can be arranged so that each metered dose of aerosol contains a predetermined amount of an active ingredient, such as the one or more of the engineered LHD proteins.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/ or adapted for any type of injection (e.g. intravenous, intraperitoneal, subcutaneous, intramuscular, intradermal, intraosseous, epidural, intracardiac, intraarticular, intracavernous, gingival, subginigival, intrathecal, intravireal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the engineered LHD protein per unit dose. In some embodiments, the predetermined amount of the the engineered LHD protein is a therapeutically effective amount of the the engineered LHD protein, effective to treat or prevent *C. difficile* or a symptom thereof. In other embodiments, the predetermined amount of the engineered LHD protein can be an appropriate fraction of the therapeutically effective amount of the active ingredient (e.g. the engineered LHD protein and/or auxiliary active agent). Such unit doses may therefore be administered once or more than once a day. Such pharmaceutical formulations may be prepared by any of the methods well known in the art.

Methods of Using the Engineered LHD Proteins and Pharmaceutical Formulations Thereof The engineered LHD proteins and pharmaceutical formulations thereof described herein can be used for the treatment and/or prevention of a disease, disorder, syndrome, or a symptom thereof in a subject. In some embodiments, the engineered LHD proteins and pharmaceutical formulations thereof described herein can be used to treat and/or prevent *C. difficile* and/or a symptom thereof in a subject.

An amount of the engineered LHD proteins and pharmaceutical formulations thereof described herein can be administered to a subject in need thereof one or more times per day, week, month, or year. In some embodiments, the amount administered can be the therapeutically effective amount of the engineered LHD proteins and pharmaceutical formulations thereof. For example, the engineered LHD proteins and pharmaceutical formulations thereof can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the engineered LHD proteins and pharmaceutical formulations thereof can be administered one or more times per week, such as 1, 2, 3, 4, 5, or 6 times per week. In other embodiments, the engineered LHD proteins and pharmaceutical formulations thereof can be administered one or more times per month, such as 1 to 5 times per month. In still further embodiments, the engineered LHD proteins and pharmaceutical formulations thereof can be administered one or more times per year, such as 1 to 11 times per year.

The engineered LHD proteins and pharmaceutical formulations thereof can be co-administered with a secondary agent by any convenient route. The secondary agent is a separate compound and/or pharmaceutical formulation from the engineered LHD proteins or pharmaceutical formulations thereof. The secondary agent can be administered simultaneously with the engineered LHD proteins or pharmaceutical formulations thereof. The secondary agent can be administered sequentially with the engineered LHD proteins or pharmaceutical formulations thereof. Suitable secondary agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

In embodiments where the engineered LHD proteins or pharmaceutical formulations thereof are simultaneously co-administered with a secondary agent, the engineered LHD proteins or pharmaceutical formulations thereof can be administered to the subject at substantially the same time as the secondary agent. As used in this context "substantially the same time" refers to administration of engineered LHD proteins or pharmaceutical formulations thereof and a secondary agent where the period of time between administration of the engineered LHD proteins or pharmaceutical formulations thereof and the secondary agent is between 0 and 10 minutes.

In embodiments where the engineered LHD proteins or pharmaceutical formulations thereof is/are sequentially co-administered with a secondary agent, the engineered LHD proteins or pharmaceutical formulations thereof can be administered first, and followed by administration of the secondary agent after a period of time. In other embodiments where the engineered LHD proteins or pharmaceutical formulations thereof is/are sequentially co-administered with a secondary agent, the secondary agent can be administered first, and followed by administration of the engineered LHD proteins or pharmaceutical formulations thereof after a period of time. The period of time between administration of the engineered LHD proteins or pharmaceutical formulations thereof and the secondary agent can range from 10 minutes to about 96 hours. In some embodiments the period of time can be about 10 minutes, about 30 minutes, about 1 hour, about 2 hours, about 4 hours, about 6 hours, about 8 hours, about 10 hours, or about 12 hours. The sequential administration can be repeated as necessary over the course of the period of treatment.

The amount of the engineered LHD proteins or pharmaceutical formulations thereof that can be administered are described elsewhere herein. The amount of the secondary agent will vary depending on the secondary agent. The amount of the secondary agent can be a therapeutically effective amount. In some embodiments, the effective amount of the secondary agent ranges from 0.001 micrograms to about 1 milligram. In other embodiments, the amount of the secondary agent ranges from about 0.01 IU to about 1000 IU. In further embodiments, the amount of the secondary agent ranges from 0.001 mL to about 1 mL. In yet other embodiments, the amount of the secondary agent ranges from about 1% w/w to about 50% w/w of the total pharmaceutical formulation. In additional embodiments, the amount of the secondary agent ranges from about 1% v/v to about 50% v/v of the total pharmaceutical formulation. In still other embodiments, the amount of the secondary agent ranges from about 1% w/v to about 50% w/v of the total secondary agent composition or pharmaceutical formulation.

In some embodiments, the engineered LHD proteins or pharmaceutical formulations thereof can be administered to a patient via an injection. Suitable methods of injection include, but are not limited to, intravenous, intraperitoneal, subcutaneous, intramuscular, intradermal, intraosseous, epidural, intracardiac, intraarticular, intracavernous, intrathecal, intravitreal, intracerebral, gingival, subginigival, intranodal, and intracerebroventricular injection. Other suitable methods of administration of the composition or formulation containing the engineered LHD proteins or pharmaceutical formulations thereof can include, but are not limited to, subcutaneous, intravenous, parenteral, and/or oral delivery. In some embodiments, the dosage of the engineered LHD proteins or pharmaceutical formulation thereof ranges from about 0.01 µg/kg bodyweight to about 1 mg/kg bodyweight.

Kits containing the Engineered LHD Proteins and/or Pharmaceutical Formulations Thereof The engineered LHD proteins or pharmaceutical formulations thereof described herein can be presented as a combination kit. As used herein, the terms "combination kit" or "kit of parts" refers to the engineered LHD proteins or pharmaceutical formulations thereof and compositions and pharmaceutical formulations thereof described herein and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

The combination kit can contain each agent, compound, pharmaceutical formulation or component thereof described herein, in separate compositions or pharmaceutical formulations. The separate compositions or pharmaceutical formulations can be contained in a single package or in separate packages within the kit. Also provided in some embodiments, are buffers, diluents, solubilization reagents, cell culture media and other reagents. These additional components can be contained in a single package or in separate packages within the kit.

In some embodiments, the combination kit also includes instructions printed on or otherwise contained in a tangible medium of expression. The instructions can provide information regarding the content of the engineered LHD proteins or pharmaceutical formulations thereof and/or other auxiliary and/or secondary agent contained therein, safety information regarding the content of the engineered LHD proteins or pharmaceutical formulations thereof and/or other auxiliary and/or secondary agent contained therein, information regarding the dosages, indications for use, and/or recommended treatment regimen(s) for the engineered LHD proteins or pharmaceutical formulations thereof and/or other auxiliary and/or secondary agent contained therein. In some embodiments, the instructions can provide directions for administering engineered LHD proteins or pharmaceutical formulations thereof and/or other auxiliary and/or secondary agent to a subject having or suspected of having *C. difficile* infection and/or a symptom thereof.

Without further elaboration, it is believed that one skilled in the art can, based on the description herein, utilize the present disclosure to its fullest extent. It is emphasized that the embodiments of the present disclosure, particularly any "preferred" embodiments, are merely possible examples of the implementations, merely set forth for a clear understanding of the principles of the disclosure. Many variations and modifications may be made to the disclosed embodiment(s) of the disclosure without departing substantially from the spirit and principles of the disclosure. All such modifications and variations are within the scope of this disclosure.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Introduction

*Clostridium difficile*, reclassified as *Clostridioides difficile* (Lawson, Citron et al. 2016), is a Gram-positive, spore-forming, anaerobic, and toxin-producing nosocomial pathogen. Since the first description of a *C. difficile*-associated disease (CDAD)-like case in 1892 (Finney 1893), *C. difficile* infection (CDI) has become a high-impact health care-associated infection throughout the world, especially in the developed countries. In the United States, *C. difficile* is listed as one of the three most urgent antibiotic resistance threats by the Centers for Disease Control and Prevention (CDC) (CDC 2013), and CDI is responsible for approximately 453,000 cases of infections and 29,000 deaths every year, with an annual economic burden ranging from $436 million to $3 billion dollars (Napolitano and Edmiston 2017). In Europe, CDI was associated with considerable short or long term disability, 8382 deaths per year (Cassini, Plachouras et al. 2016), and an annual economic burden of €3 billion euro (Reigadas Ramirez and Bouza 2018).

Currently, oral antibiotics such as metronidazole, vancomycin and fidaxomicin is still recommended treatment for CDI (Debast, Bauer et al. 2014, McDonald, Gerding et al. 2018). However, *C. difficile* isolates with significantly reduced susceptibility, and even resistance to these recommended antibiotics have been frequently identified and reported (Spigaglia 2016, Peng, Addisu et al. 2017, Peng, Jin et al. 2017). In this regard, development of novel antibiotics and/or alternative treatment strategies for CDI receives increasing attentions nowadays. A previous study showed that a prophage lysin PlyCD and its catalytic domain PlyCD1-174 had good lytic activities against specific *C. difficile* strains (Wang, Euler et al. 2015). In addition to phage lysin, human alpha-defensin 5 (HD5) can also effectively lyse hypervirulent *C. difficile* strains (Furci, Baldan et al. 2015). Here, we report the generation of a novel fusion protein containing bacteriophage lysin and human defensin, which showed potent lytic activity in vitro, and was effective in treatment of CDI in mice.

Materials and Methods

Bacterial Strains

*C. difficile* strains R20291 (ribotype 027), M120 (ribotype 078), VPI 10463 (ribotype 087; ATCC 43255), CD630 (ribotype 012), LC693 (ribotype unknown, ST201), and 1377 (ribotype 012) were used in this study. Strains M120 and VPI 10463 were provided by Dr. Joseph A. Sorg from Texas A&M University. Strains R20291 and CD630 were provided by Dr. Abraham L. Sonenshein from Tufts University. Strains 1377 and LC693 were epidemic clinical strains in China (Li, Liu et al. 2015, Peng, Liu et al. 2017). Detailed information of these *C. difficile* strains is listed in Table 1.

TABLE 1

| Information of *C. difficile* strains used in this study | | | | |
|---|---|---|---|---|
| Strain | Ribotype | Sequence type | Toxin profile | Country of isolation |
| R20291 | 027 | ST1 | A+B+CDT+ | United Kingdom |
| M120 | 078 | ST11 | A+B+CDT+ | Ireland |
| VPI 10463 | 087 | ST46 | A+B+CDT– | Canada |
| CD630 | 012 | ST54 | A+B+CDT– | Switzerland |
| LC693 | Undetermined | ST201 | A+B+CDT+ | China |
| 1377 | 012 | ST54 | A+B+CDT– | China |

Note:
CDT (binary toxin of *C. difficile*)

Construction and Expression of the Fusion Protein LHD and Catalytic Domain (LCD) of *C. difficile* Phage phiC2.

The gene sequence coding for catalytic domain (LCD, 179 aa) of *C. difficile* phage phiC2 (NCBI reference sequence NC_009231), and the fusion gene sequence (LHD) coding for LCD, a 3-repeating unit linker (GGGGS)$_3$ and human alpha-defensin 5 (HD5) (32 aa) (Furci, Baldan et al. 2015) were synthesized, and optimized for expression in *E. coli* by GenScript. The synthesized fusion gene sequence, and gene sequence coding for LCD were cloned into pET-28a (+) using restriction enzymes BamHI and HindIII. The recombinant plasmids pET-LHD and pET-LCD were introduced into *E. coli* BL21DE3 for protein expression. The resultant proteins LHD and LCD carry an N-terminal His-tag. For protein induction and expression, *E. coli* BL21DE3 cells carrying pET-LHD or pET-LCD were inoculated into LB broth containing 50 μg/mL kanamycin, and incubated at 37° C. with shaking to mid-log phase (OD$_{600}$ values between 0.6 and 0.8), followed by addition of 0.5 mM IPTG to induce protein expression for 2-3 hrs. To determine the best inducing condition for each of the proteins, bacteria with IPTG were grown at 15° C. for overnight; 20° C., overnight; 25° C., overnight; 30° C., 3 hrs; 30° C., 4 hrs; 37° C., 3 hrs; and 37° C. for 4 hrs.

After induction, bacterial culture was centrifuged, and the pellets were re-suspended in a lysis buffer (Buffer A: 0.5 M NaCl+0.02 M Na$_3$PO$_4$; PH=7.5). Then, the bacterial suspension was sonicated, and centrifuged at 20,000 rpm for 40 min. The supernatant recovered after centrifugation was filtered through a 0.45-μm membrane, the proteins were purified using a GE Healthcare HisTrap™ HP Nickel column (Uppsala, Sweden) with 5%, 10%, 15%, 30%, and 100% of elusion buffer (Buffer B: Buffer A+500 mM imidazole, PH=7.5). The purified proteins were dialyzed at 4° C. against PBS overnight, concentrated using Centricon centrifugal filter (Millipore), and stored in PBS at –80° C. for further study. The protein purity was analyzed by SDS-PAGE, and concentration determined by nanodrop.

Determination of Lytic Activity of Proteins LHD and LCD Against *C. difficile* Strains.

The lytic activity of proteins LHD and LCD against *C. difficile* strains was determined as previously described (Wang, Euler et al. 2015). Briefly, *C. difficile* strains were cultured in an anaerobic chamber to mid-log phase, and the bacterial pellets were harvested by centrifugation at 3000×g for 5 min. Pellets were washed twice and re-suspended in sterilized ddH$_2$O, and resuspensions were not buffered. Prior to tests, bacterial optical density at 600 nm (OD$_{600}$) was adjusted to approximately 0.8-1.0. Proteins LHD and LCD were added into the cell re-suspension with the final concentration of 200 μg/ml. The drop in OD$_{600}$ at 37° C. was measured every 10 minutes for 60 min~90 min. Bacterial re-suspension with sterilized water was also set as a control. Three repeats were included in each test.

The minimum inhibitory concentrations (MICs) of LHD and LCD were determined using the protocol of Wiegand, et al. (Wiegand, Hilpert et al. 2008) with some modifications, as described previously (Gilmer, Schmitz et al. 2017). In brief, strain R20291 was grown in BHIS and adjusted to ~5×10$^5$ cells/ml in BHIS, and distributed into the wells of a 96-well round bottom polystyrene microtiter plate. In the wells of each row, either sterile-filtered lysin or control vehicle (metronidazole, vancomycin and fidaxomicin) was added with a final concertation varied from 200 μg/ml to 0.19 μg/ml (2-fold dilution) (Wiegand, Hilpert et al. 2008). The plates were incubated at 37° C. for 18 h. The MIC was "the lowest or minimum concentration of lysin or control vehicle that prevented the formation of a cell pellet (a measure of growth) on the bottom of the wells" (Gilmer, Schmitz et al. 2017). The MICs were also confirmed by measuring the OD$_{600}$ values using a Bio-Rad plate reader (Bio-Rad, Hercules, CA).

To determine the optimal pH values for the lytic activity of LHD against *C. difficile*, optical drop assays described above were performed with *C. difficile* strain R20291 in buffers of different pH (pH 6.0, 7.0, and 8.0).

Determination of Inhibitory Activity of LHD Against *Clostridium difficile* Toxin B (TcdB).

It was reported that the human defensin protein HD5 (HD) could inhibit TcdB (Giesemann, Guttenberg et al. 2008). Therefore, we evaluated the inhibitory effects of LHD and HD on TcdB. Briefly, CT26 cells in 12-well plates were exposed to LHD, synthesized HD or PBS at 750 ng/ml (50 times of TcdB concentration) for 1 hr, followed by exposure to TcdB at 15 ng/ml for 5 hrs. Total cell lysates were subjected to 12% SDS-PAGE separation, and transferred onto a Nylon membrane. Following blocking for 1 hr at room temperature with 5% skim milk, the membrane was incubated overnight at 4° C. with RAC1 antibody (1:1000, Cat: 610650, BD Biosciences) and β-actin antibody (1:10000, Cat: A5441, Sigma-Aldrich). After washing PBST (PBS with 0.1% Tween), the membrane was incubated with horseradish peroxidase-conjugated secondary antibody goat anti-mouse (Cat: ab97023, goat anti-rabbit, IgG, 1:3000, Abcam), the antibody-reactive bands were revealed by enhanced chemiluminescence detection on Hyperfilm (Thermo Fisher Scientific, Waltham, MA).

Glucosyltransferase (GT) activity of TcdB was also measured by its ability to glucosylate Rho GTPase Rac1 in cell lysates (Zhang, Shi et al. 2013). CT26 cell pellets were resuspended in a reaction buffer (50 mM HEPES, pH 7.5, 100 mM KCl, 1 mM MnCl$_2$ and 2 mM MgCl$_2$), and lysed by passing through a 30 G needle for 40 times. After centrifugation (167,000 g, 3 min), the supernatant was used as a cytosolic fraction (protein concentration 2.5 mg/ml). To perform the glucosylation assay, the cytosolic fraction was incubated with TcdB at 15 ng/ml (with or without LHD or HD at 750 ng/ml) at 37° C. for 60 min. The reaction was terminated by adding SDS-sample buffer, and samples were heated at 100° C. for 5 min before loading on a 12% SDS-PAGE gel. Western bot analysis was performed as described above to detect non-glucosylated Rac1.

Evaluation of Treatment Efficacy of LHD in the Mouse Model of CDI.

Figure 6:
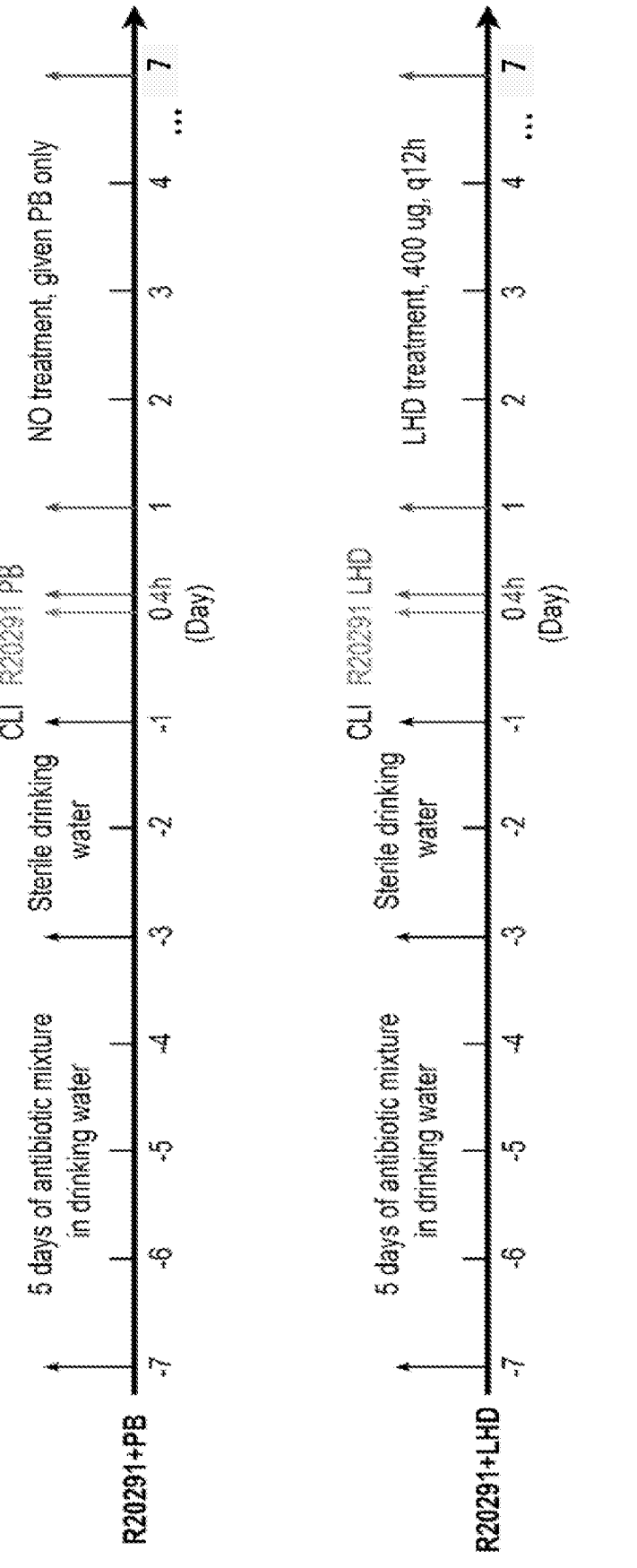
FIG. 6 shows experimental schemes for evaluation of LHD treatment efficacy in mouse model of CDI. After 5 days of antibiotic pretreatment, mice were given autoclaved water for 2 days, followed by a single dose of clindamycin (10 mg/kg) intraperitoneally, 1 day before (day-1) challenge with *C. difficile* R20291 spores by gavage (day 0). The first group (R20291+PB) was infected with $10^6$ *C. difficile* R20291 spores on day 0, and was given PBS (PB) by gavage at 4 h after spore gavage, followed by administration of PB by gavage twice a day from the first day (day 1) to the seventh day (day 7) after spore gavage. The second group (LHD+R20291) was given 400 µg LHD by gavage at 4 h after spore gavage, followed by treatments of 400 µg LHD by gavage twice a day from day 1 to day 7 after spore gavage.

C57BL/6 mice (6-week-old) were purchased from Charles River Laboratories, MA. The mice were housed in groups of 5 animals per cage under the same conditions. All studies followed the Guide for the Care and Use of Laboratory Animals of the National Institutes of Health, and were approved by the Institutes Animal Care and Use Committee (IACUC) at University of South Florida under the animal protocol number 1S00003756. Mouse model of CDI was established as described previously (Zhang, Zhao et al. 2015). The experimental design is illustrated in FIG. 6. Briefly, twenty BL6/C57 female mice were divided into two groups (n=10). Before challenge, mice were pre-treated with antibiotics mixture (ampicillin (200 mg/kg), kanamycin (40 mg/kg), gentamicin (3.5 mg/kg), colistin (4.2 mg/kg), metronidazole (21.5 mg/kg) and vancomycin (4.5 mg/kg)) in drinking water for five days. After that, all mice were given autoclaved water for 2 days, followed by a single dose of clindamycin (10 mg/kg) intraperitoneally 1 day before (day-1) challenge with *C. difficile* R20291 spores at 10$^6$ by gavage (day 0). At 4-hr post infection, one group of mice (R20291+LHD) were given a dose of 400 μg LHD in 200 μL of PBS by gavage, and another group of mice (R20291+PB) received sterilized PBS as control. From the first day (day 1) to the seventh day (day 7) after infection, mice were given a dose of 400 μg LHD or PBS by gavage twice a day. Weight changes, diarrhea, and survivals of the mice were recorded during the 7-day monitoring period. Fecal samples from mice were collected at days 0, 1, 3, 5, and 7 post challenge for quantitating *C. difficile* spores and TcdA/TcdB concentration.

To appreciate the stability and activity of LHD in the mouse intestine, LCD protein was incuated with freshly prepaerd mouse intestinal contents for 15 min, 30 min and 60 min, and retrived by centrifugation. Lytic activities of LHD treated with intestinal contents were determined on strain *C. difficile* R20291 as described above.

Quantification of *C. difficile* Spores from Mouse Feces.

Fecal samples were collected on days 1, 3, 5, 7 post-infection. 50 mg of feces were dissolved with 500 µl sterile MilliQ water for 16 h at 4° C., and then treated with 500 µl of purified ethanol (Sigma-Aldrich) for 60 min at room temperature to kill vegetative cells. Samples were vortexed, serially diluted and plated onto selective medium supplemented with taurocholate (0.1% w/v), Cefoxitin (16 µg/mL), L-cycloserine (250 µg/mL). The plates were incubated anaerobically at 37° C. for 48 h, colonies counted and results expressed as the CFU/gram of feces.

Quantitation of *C. difficile* Toxins in Mouse Feces.

After challenges with *C. difficile* spores, feces were collected and dissolved in an equal volume (g/ml) of sterile PBS containing protease inhibitor cocktail and the supernatants were collected after centrifugation and stored at −80° C. TcdA/TcdB concentrations in the fecal samples of Tcd169 or Tcd169F1-immunized mice were determined by ELISA. Briefly, 96-well Costar microplates were coated with 100 µl of anti-TcdA antibody (1 µg/ml) and anti-TcdB antibody (1 µg/ml) overnight in phosphate-buffered saline (PBS) at 4° C. On the next day, each well was blocked with 300 ul of blocking buffer (PBS+5% dry milk) at RT for 2 hrs. Next, standards and samples were added to each well (100 µl) in duplicate and incubated for 90 min at 25° C. After another set of washes, HRP-chicken anti-*C. difficile* Toxin A or B (1:5,000 dilution in PBS, Gallus Immunotech, Shirley, MA) was added to wells for 30 min at RT. A final set of 3 washes preceded the addition of the TMB Microwell Peroxidase Substrate for 20 minutes at RT in the dark. The reaction was stopped with 2 N $H_2SO_4$, and the absorbance was measured using a plate reader at 450 nm, and the ELISA was analysed by a spectrophotometer at 450 nm utilizing BioTek Gen5 Version 2.0 Data Analysis Software.

Statistical Analysis.

When comparing results for two groups, student's unpaired t-test was used for statistical significance; when comparing the results of more than two groups, ordinary one-way analysis of variance (ANOVA) with post-hoc analysis by Dunnett's test was used. Differences were considered statistically significant if $P<0.05$ (*). All statistical analyses were performed using GraphPad Prism software.

Results

Design and Expression of the Lysin-Human Defensin Fusion Protein, LHD.

The engineered bacteriophage lysin-human defensin fusion protein LHD was designed by linking the catalytic domain (LCD, 179aa) of a lysin protein from phage phiC2 (NCBI reference sequence NC_009231) and human alpha-defensin 5 (HD5, designated HD in this paper) (Furci, Baldan et al. 2015) with a 3-repeating unit linker ("GGGGS")$_3$ (FIGS. 1A-1B). Phage phiC2 is present in the majority of human isolates of *C. difficile* (Roy Chowdhury, DeMaere et al. 2016). A LCD from phage phiC2 was used as part of the LHD. There was 34% identity in amino acid sequence between LCD and PlyCD$_{1174}$. The predicted molecular weight of the lysin-human defensin fusion protein LHD was approximately 24.4 kDa with a PI of 9.1.

The DNA sequences of LHD and LCD were cloned into the protein expression vector pET-28a (+). The recombinant plasmids were transformed into the expression host *E. coli* BL21 cells for protein induction and expression. After induction at 37° C., both LHD and LCD seemed expressed in inclusion bodies, since no LHD or LCD could be detected on SDS-PAGE gels from supernatants recovered from centrifugation of the sonicated bacterial pellets (data not shown).

Figures 2A, 2B, 2C:
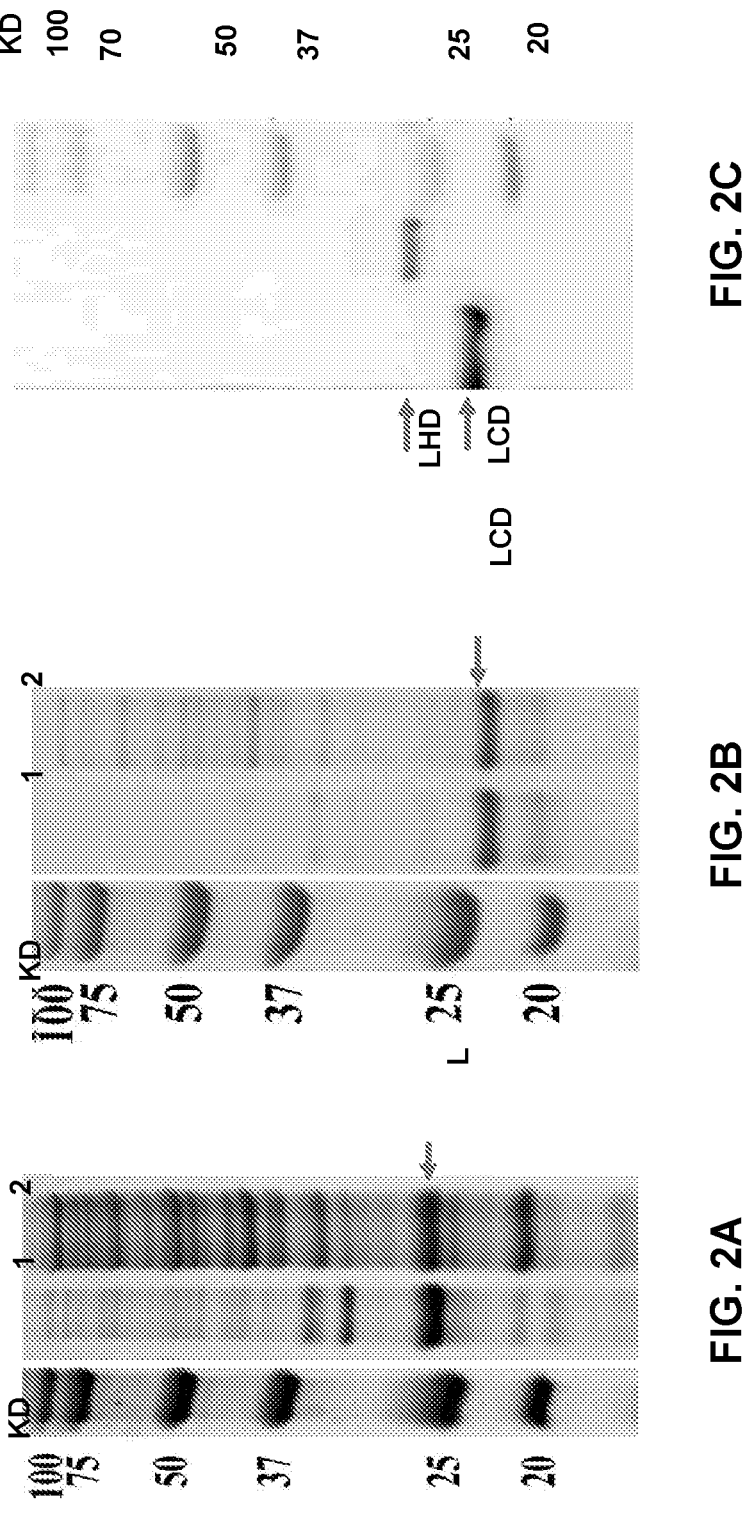
FIGS. 2A-2C can demonstrate Purification of protein LHD and LCD.
Figure 3A:
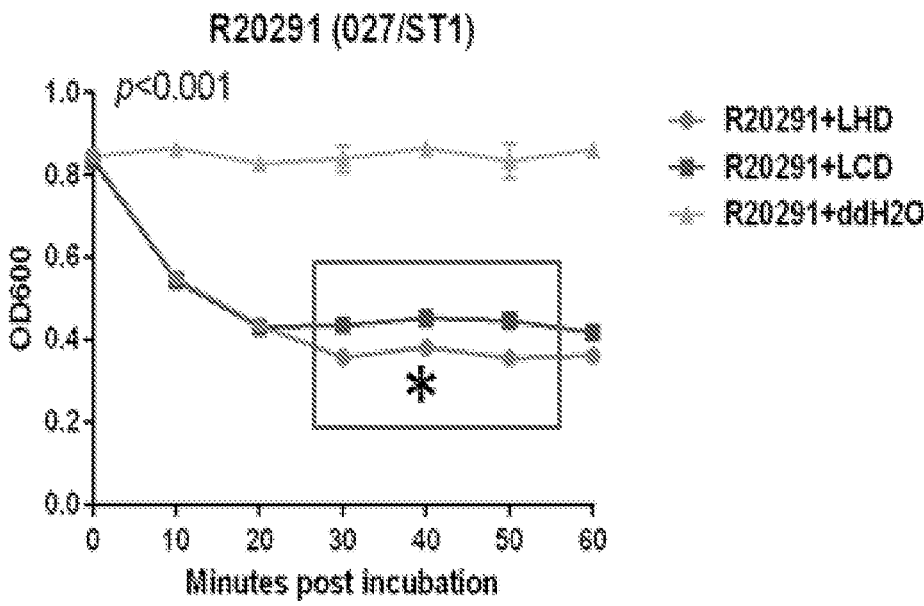
FIGS. 3A to 3F contains graphs demonstrating the lytic activity of LHD on different types of *C. difficile* strains. The lysin catalytic domain LCD was included as a control. Lytic activity of LHD was significantly higher than that of LCD at the time points marked in red boxes ($p<0.05$). $p<0.001$ between groups "*C. difficile* strain+LHD" and "*C. difficile* strain+$H_2O$". Data are present as "Mean±SD". Experiments were repeated 3 times, and representative data were shown.
Figure 3B:
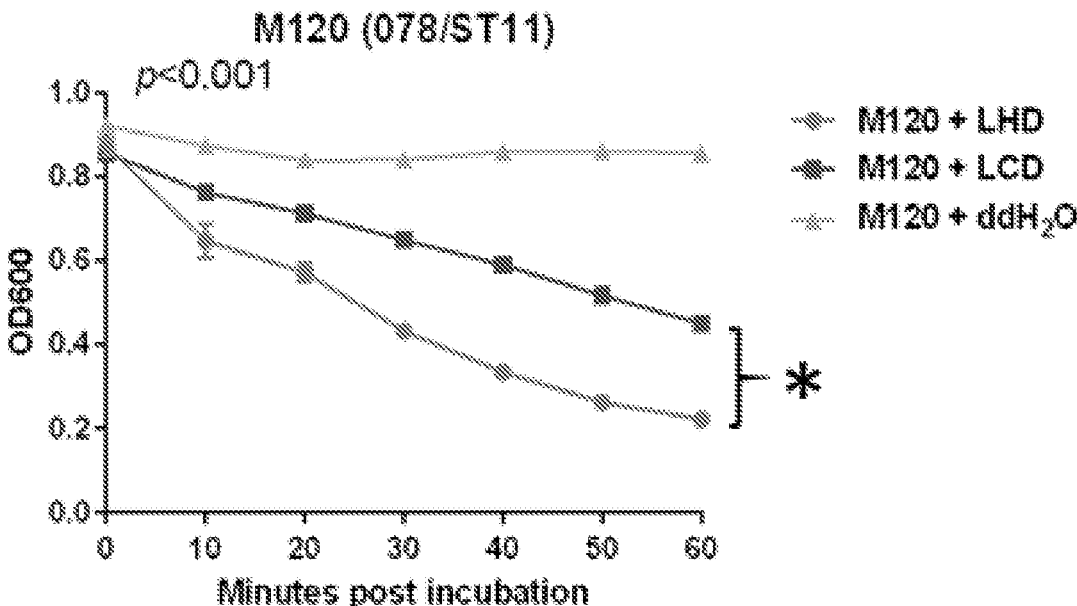
Figure 3C:
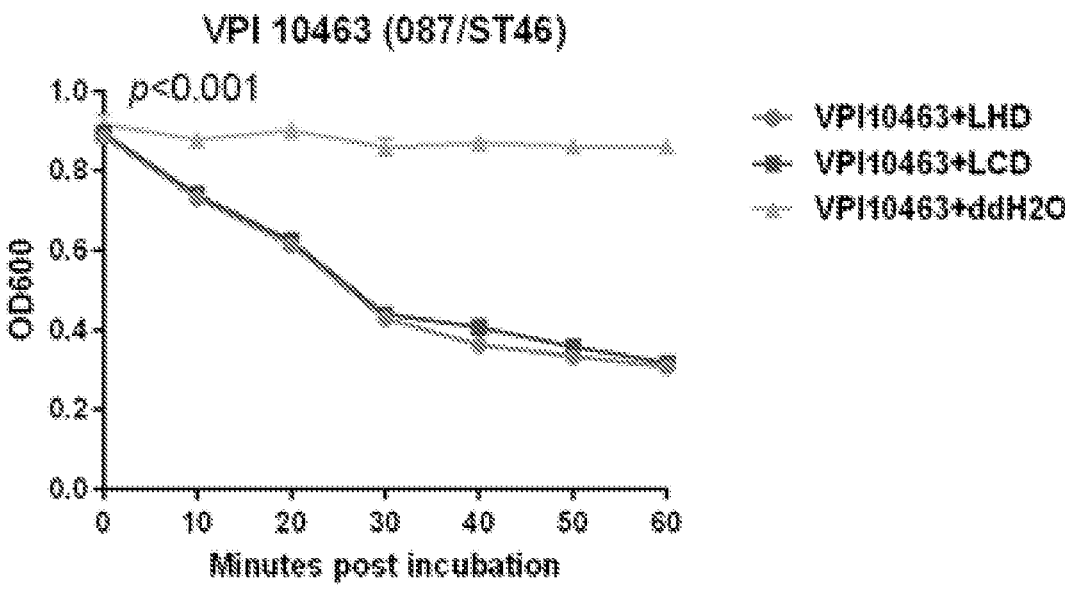
Figure 3D:
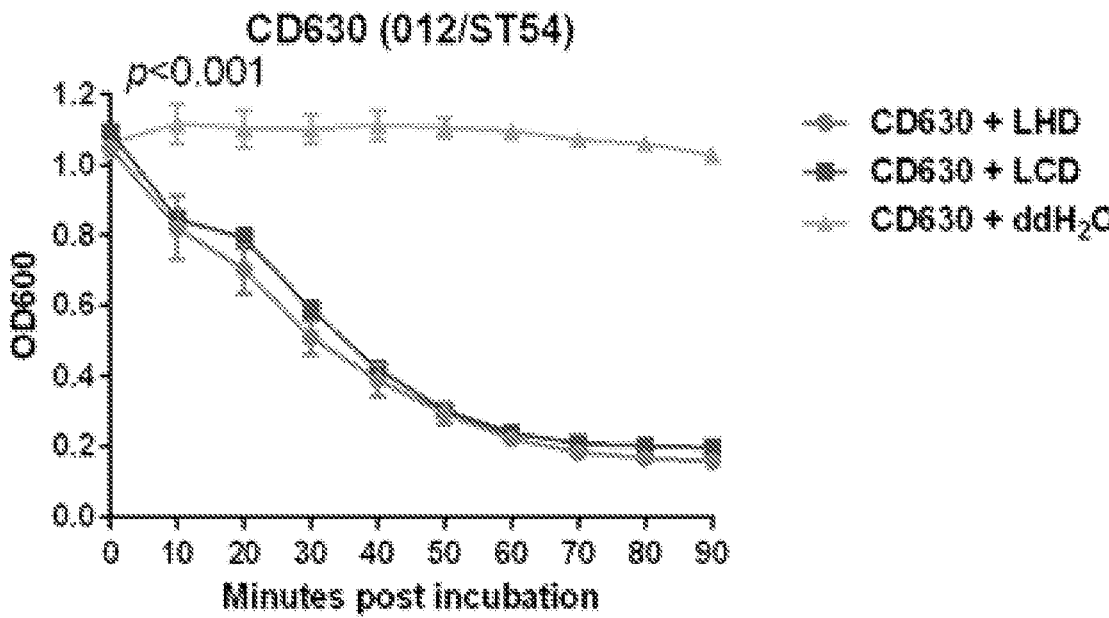
Figure 3E:
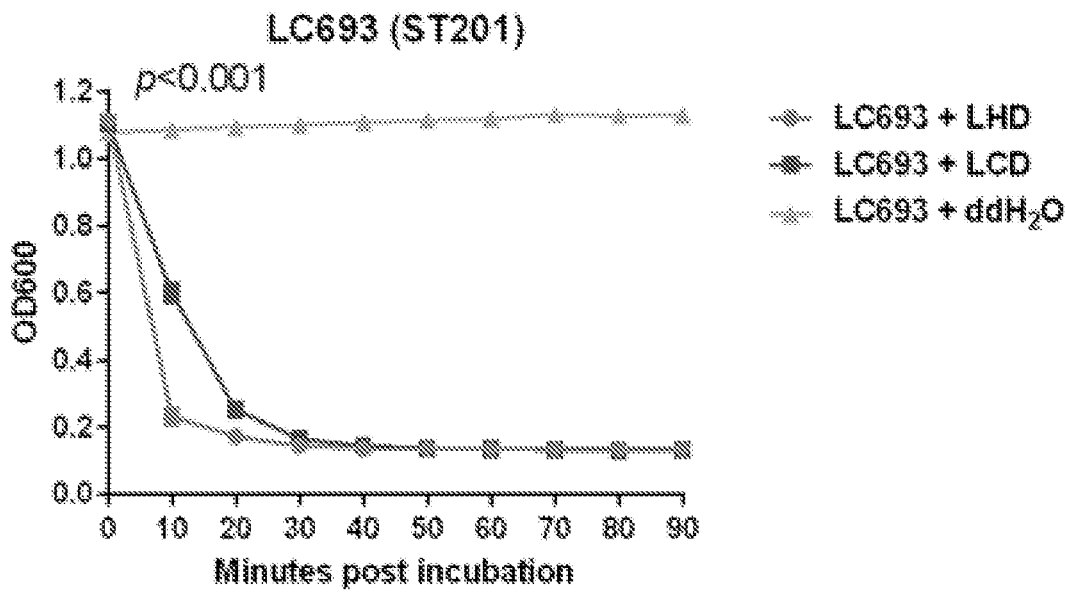
Figure 3F:
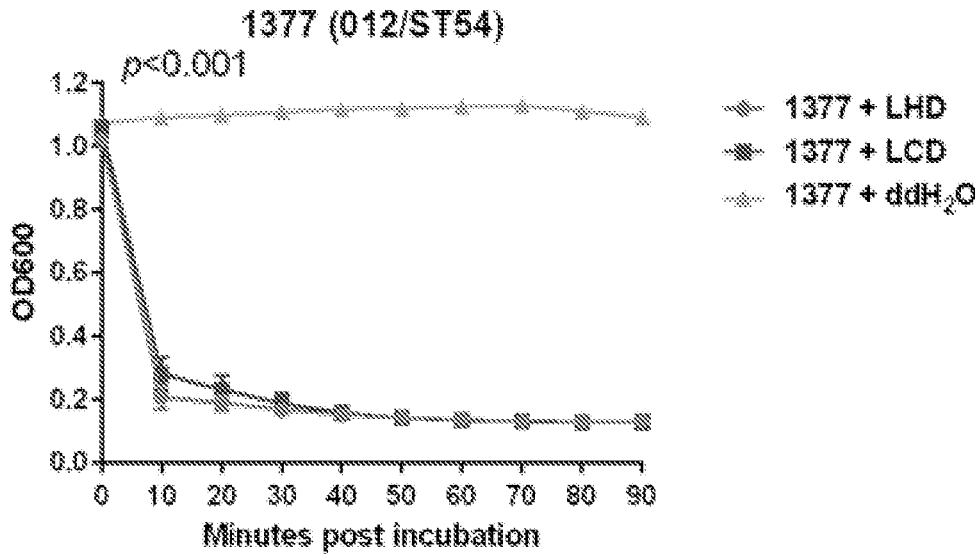

After an overnight induction at 15° C., protein LHD was detected in the supernatant after centrifugation of the sonicated bacterial pellets (FIG. 2A), indicating some portions of expressed LHD were properly folded. When induced at 30° C. for 3 h, protein LCD was well expressed and was also detected in the supernatant after centrifugation of the sonicated bacterial pellets (FIG. 2B). Proteins LHD and LCD carry an N-terminal His-tag. After purification of LHD and LCD using GE Healthcare HisTrap™ HP Nickel column, the purity of the proteins was analyzed on SDS-PAGE gels, and the results showed that both purified proteins were 95% pure (FIG. 2C).

Lytic Activity of LHD and LCD on *C. difficile* Clinical Strains.

Initially, the lytic activity of LCD and LHD was determined on a *C. difficile* 027 strain, R20291, including HD5 as a control. The optical drop assays showed that both LHD and LCD had potent lytic activities on R20291 at a concentration of 200 µg/ml, with LHD displaying a better lytic activity (FIG. 3). While HD5 also showed moderate lytic activity compared to strain R20291 treated with ddH2O), it was much less potent than both LHD and LCD in lysing strain R20291 cells (FIG. 3). It was also determined if LHD or LCD is also potent against other ST type of epidemic *C. difficile* strains. The lytic activities of LHD/LCD on strains M120 (078/ST11), VP110463 (087/ST46), CD630 (012/ST54), LC693 (ST201), a novel binary toxin-positive *C. difficile* strain associated with severe diarrhea in China) (Peng, Liu et al. 2017) and 1377 (012/ST54, an epidemic strain in Xiangya hospital in China) were also examined. Both LHD and LCD proteins showed potent lytic activities on different types of clinical epidemic strains (FIG. 3) with LHD being slightly more potent on strains VP110463, CD630, LC693 and 1377. Interestingly, LHD was more potent than LCD on strain M120 ($p<0.05$, FIG. 3). More impressively, LHD and LCD rapidly and drastically lysed strains LC693 and 1337, two epidemic *C. difficile* strains in China, in 10-20 minutes (FIG. 3).

To test the minimum inhibitory concentration (MIC) of LHD protein, optical drop assays were performed using a series of 2-fold-diluted protein LHD (from 200 µg/ml to 0.19 µg/ml) to lyse a *C. difficile* R20291. The results showed that LHD protein could lyse the bacteria at a concentration as low as 0.78 µg/ml (Table 2). The MIC of the lysin catalytic domain LCD was 1.56 µg/ml, while the MICs of the three treatment antibiotics for CDI including metronidazole, vancomycin, and fidaxomicin were 4 µg/ml, 4 µg/ml, and 0.25 µg/ml, respectively (Table 2).

TABLE 2

| Minimum inhibitory concentrations (MIC) of different anti-*C. difficile* agents tested on strain R20291 | | | | | |
|---|---|---|---|---|---|
| Agents | LHD | LCD | Metronidazole | Vancomycin | Fidaxomicin |
| MIC (µg/ml) | 0.78 | 1.56 | 4 | 4 | 0.25 |

Figure 4:
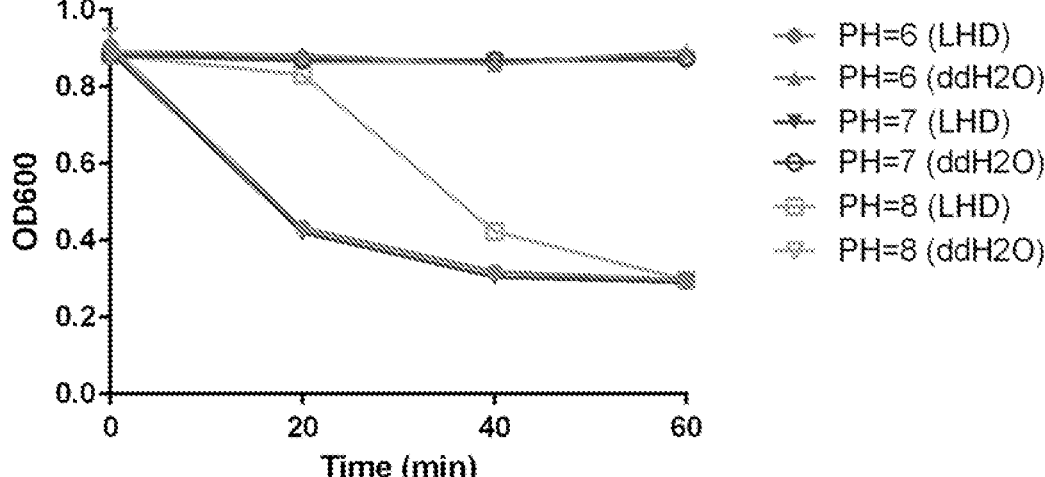
FIG. 4 shows a graph that can demonstrate the lytic activity of LHD on *C. difficile* R20291 in different pH conditions. Prior to tests, bacterial optical density at 600 nm ($OD_{600}$) was adjusted to approximately 0.8-1.0. Protein LHD was added into the cell re-suspension with the final concentration of 200 µg/ml. The drop in $OD_{600}$ at 37° C. was measured once per 20 minutes for 60 min. Bacterial re-suspension with sterilized water was also set as a control. Data are present as "Mean±SD". Experiments were repeated 3 times, and representative data were shown.
Figure 10:
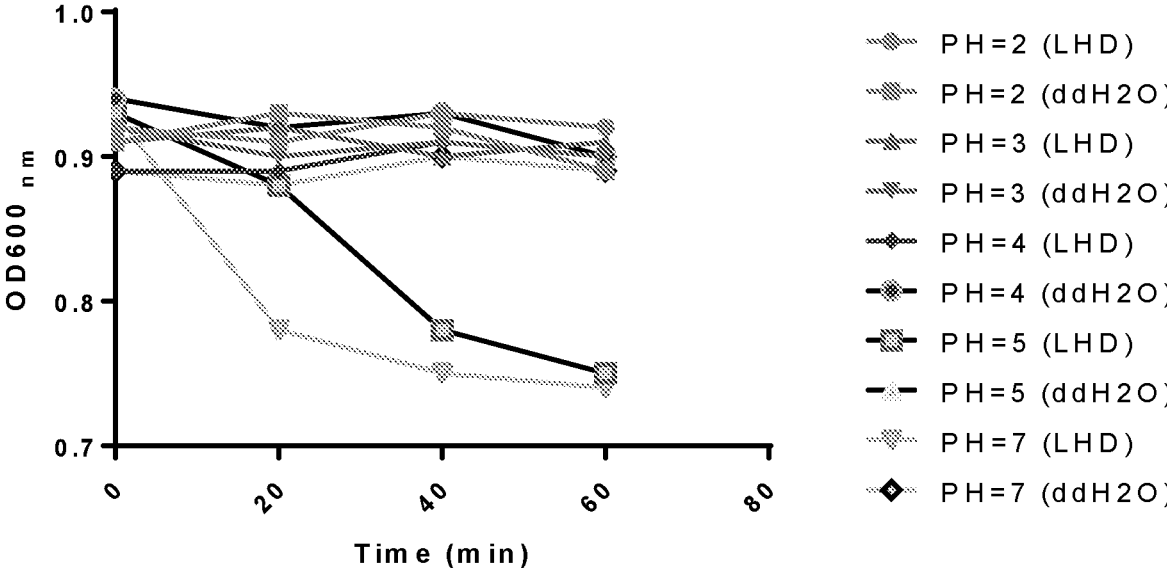
FIG. 10 shows a graph that can demonstrate the lytic activity of LHD on *C. difficile* R20291 in different pH conditions (pH 2-5). Prior to tests, bacterial optical density at 600 nm ($OD_{600}$) was adjusted to approximately 0.8-1.0. Protein LHD was added into the cell re-suspension with the final concentration of 100 µg/ml. The drop in $OD_{600}$ at 37° C. was measured once per 20 minutes for 60 min. Bacterial re-suspension with sterile water was also set as a control. Experiments were repeated 3 times, and representative data were shown.

To test the pH sensitivity, the lytic activity of LHD against strain R20291 was measured at different pH conditions. As shown in FIG. 4, LHD (200 µg/ml) lysed strain R20291 more efficiently at PHs of 6 and 7. LHD was still partially active at PH of 5, but lost almost all activity at PHs of 2, 3, and 4 (FIG. 10).

LHD Inhibits Cytotoxicity of TcdB.

Figure 5A:
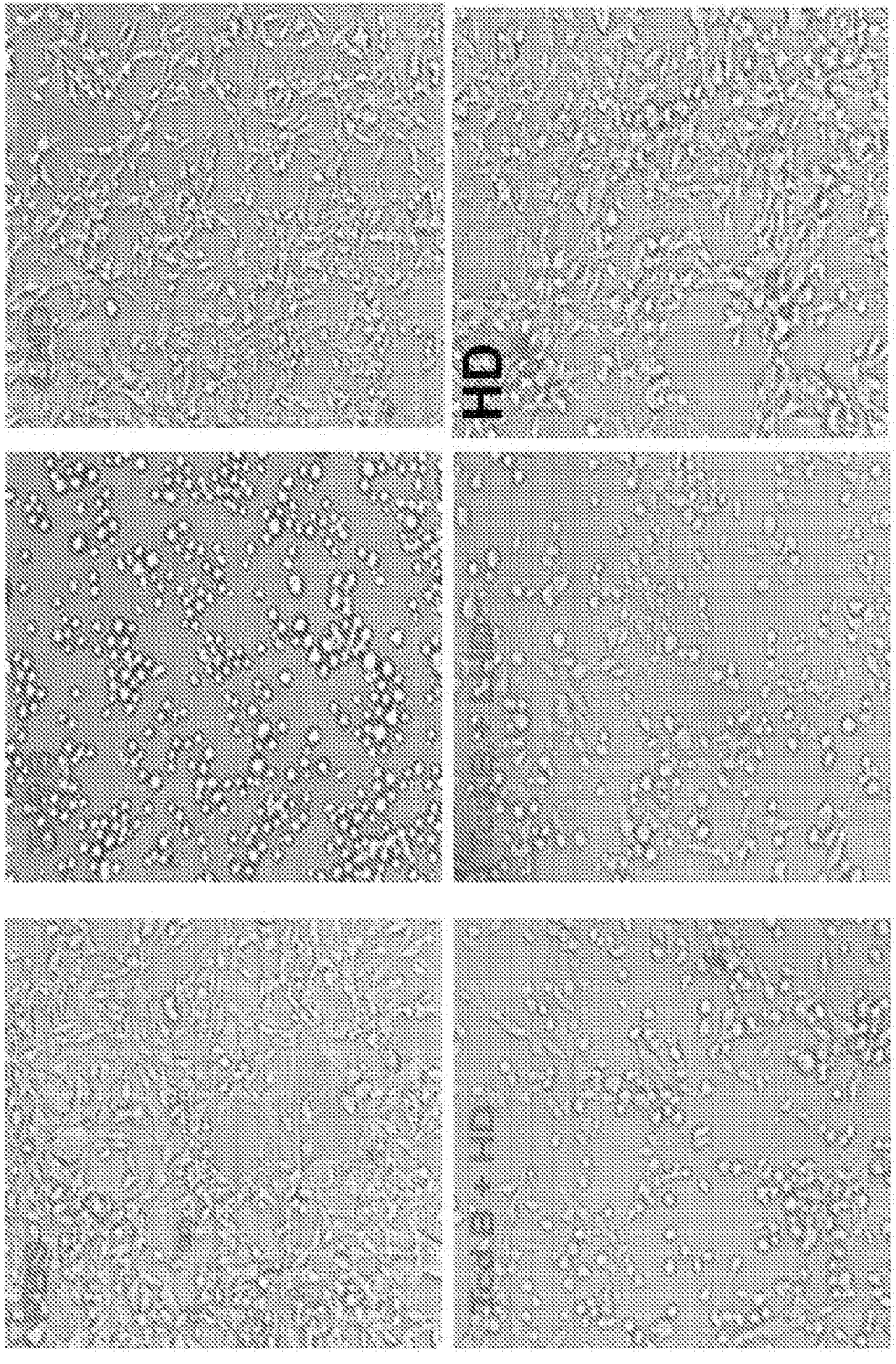
FIGS. 5A-5C show various microscopic images, blot images, and graphs that can demonstrate that LHD inhibits cytotoxicity of TcdB.
Figure 5B:
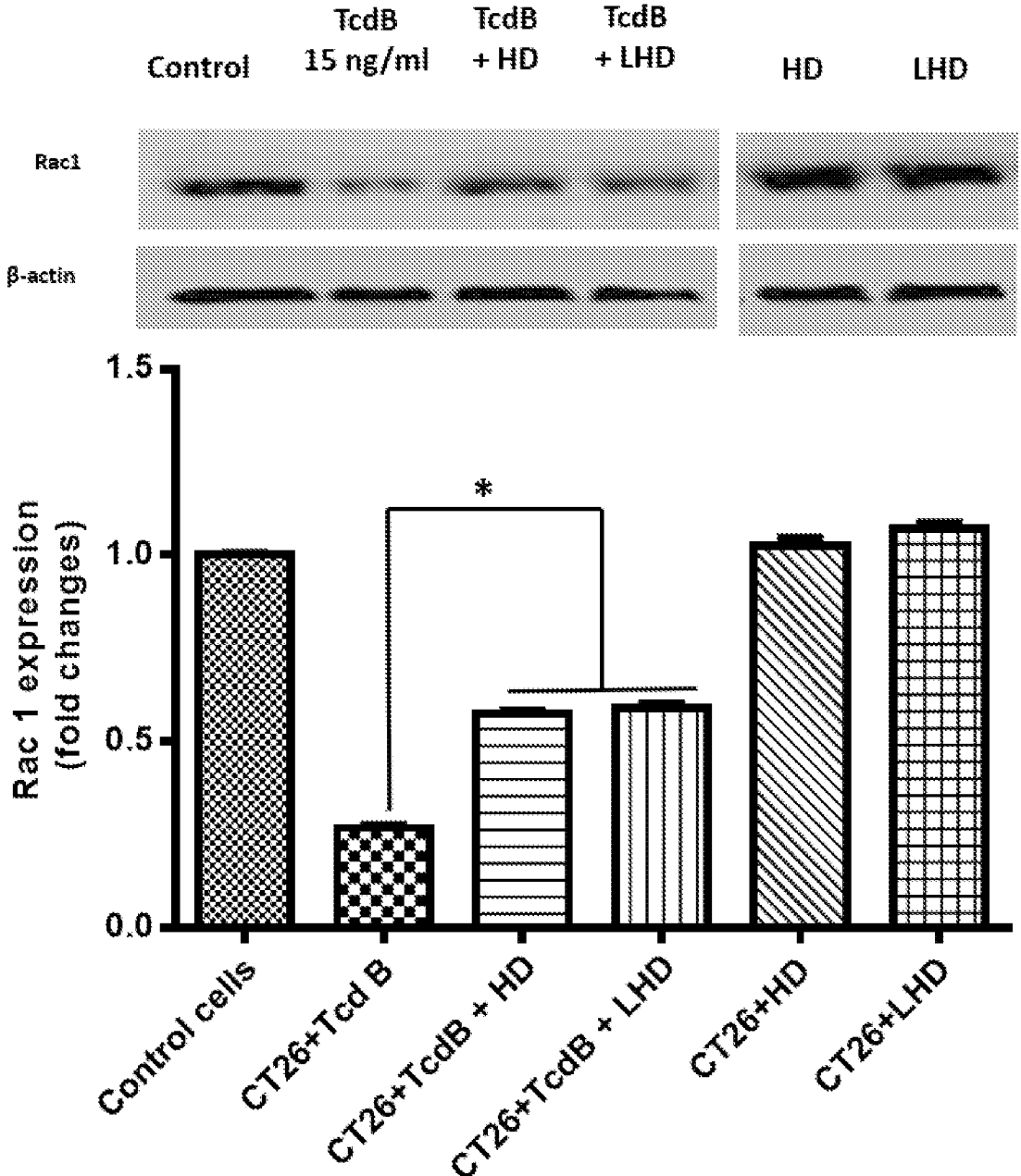

TcdB has four domains including the N-terminal catalytic glucosyltransferase domain (GT), the autoproteolytic cyste- ine proteinase domain (CPD), the central translocation domain (TM), and the C-terminal receptor-binding domain (RBD). In the host cells, the CPD domain cleaves GTD off the TcdB, releasing GTD into the cytosol, where GTD glucosylates Rho GTPases including RhoA, CDCl42, and Rac1 (Aktories, Schwan et al. 2017). The CPD-mediated TcdB autocleavage is induced by Inositol hexakisphosphate (InsP6) in vivo and in vitro (Aktories, Schwan et al. 2017). It was reported that the human defensin protein HD5 (des- ignated HD in this paper) could inhibit TcdB (Giesemann, Guttenberg et al. 2008). To examine if LHD carries the anti-TcdB function, CT26 cells were pre-treated with LHD, HD at 750 ng/ml or PBS as control for 1 hr, followed by exposure to Tcd B at 15 ng/ml for 5 hrs. The results showed that a pre-treatment of LHD or HD decreased cell rounding caused by TcdB (FIG. 5A). Western-blot analysis of non- glucosylated Rac1 in cells showed that exposure to TcdB significantly decreased the expression of non-glucosylated Rac1 in cells, as a readout of cytotoxicity of TcdB (FIG. 5B). As expected, HD inhibited the cytotoxicity of TcdB. The expression of non-glucosylated Rac1 had a significant increase when the cells received a pre-treatment of LHD prior to exposure to TcdB, indicating that LHD can inhibit cytotoxicity of TcdB as HD does by interfering with gluco- syltransferase activity of TcdB.

Figure 5C:
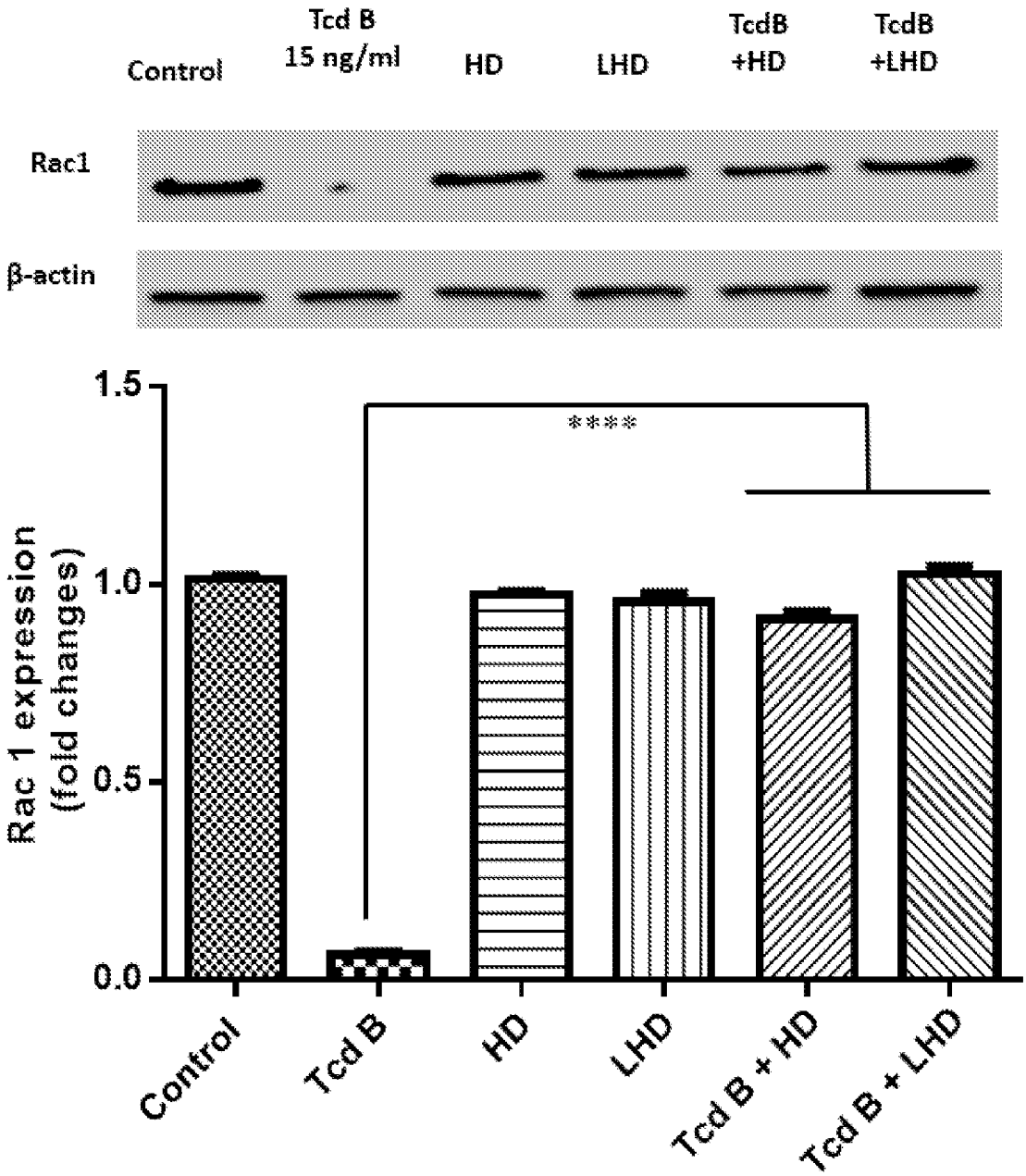

To exclude the possibility that LHD or HD may interfere with TcdB binding rather than glucosyltransferase activity of TcdB, cytosolic factions of CT26 cells were used as Rac1- containing substrates to confirm that HD or LCD could indeed inhibit glucosyltransferase activity of TcdB. Cytoso- lic fractions of CT26 cells were exposed to TcdB (15 ng/ml) in the absence or presence of HD (750 ng/ml) or LHD (750 ng/ml) for 1 hr. As shown in FIG. 5C, both HD and LCD significantly inhibited glucosyltansferase activity of TcdB to a similar extent, indicating the fused HD portion in LHD is comparable with "free" LHD in inhibiting TcdB glucosy- lation activity.

LHD is Effective in the Treatment of CDI in Mice.

To evaluate the treatment efficacy of LHD in mouse model of CDI, 20 of BL6/C57 mice were divided into two groups (n=10). One group was infected with *C. difficile* R20191 spores and treated with LHD, and the other group was infected with R20191 spores and treated with PBS as control. The experimental scheme and treatment plan are illustrated in FIG. 6.

Figure 7A:
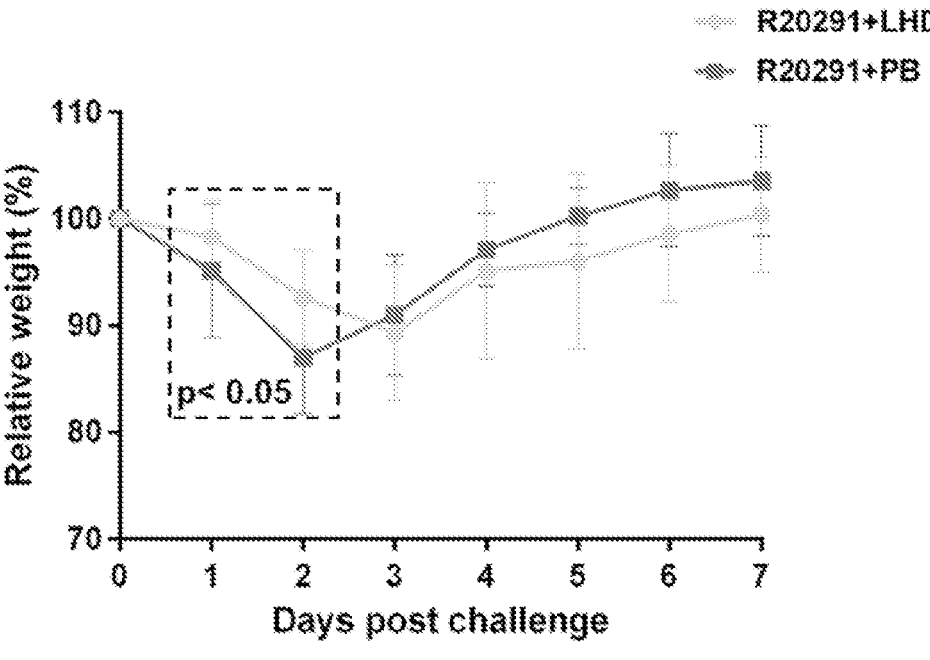
FIGS. 7A-7D can demonstrate that LHD can be effective in the treatment of CDI in mice. Twenty BL6/C57 mice were divided into two groups (n=10). One group of mice was infected with *C. difficile* R20291 spores and treated with LHD, and the other group was infected with R20291 spores and treated with PBS as control. The experimental scheme and treatment plan is illustrated in FIG. 2, and described in Methods and Materials. Weight changes (FIG. 7A), percentage of diarrhea (FIG. 7B) and (FIG. 7C), survivals of two group mice (FIG. 7D) were plotted. Mice in in group "R20291+LHD" lost significantly less weight in postinfection days 1 and 2 (p<0.05, marked in dash box region) (FIG. 7A)
Figure 7B:
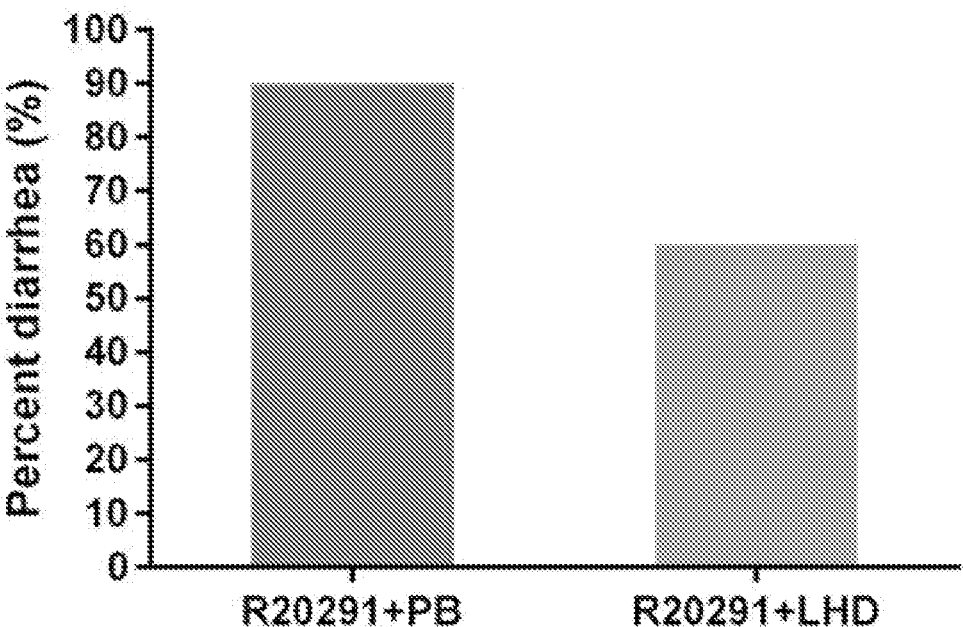
Figure 7C:
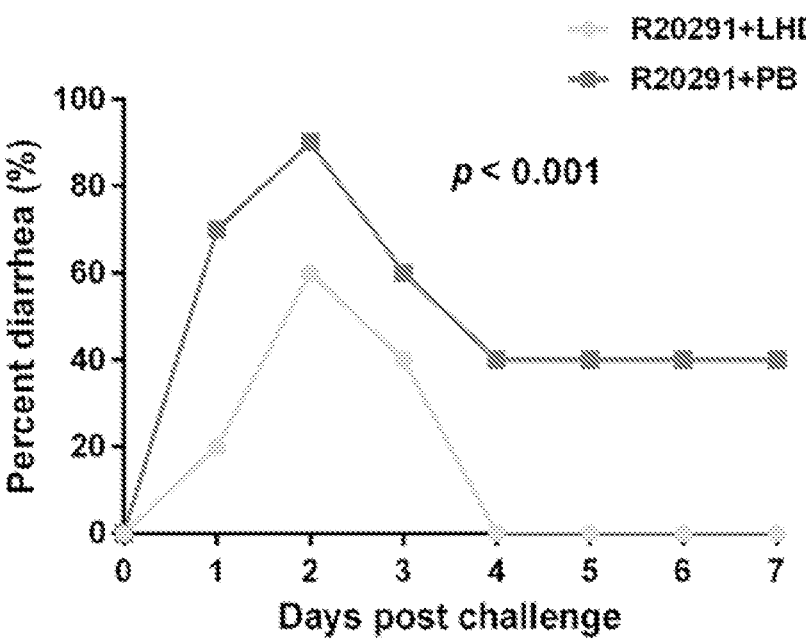
Figure 7D:
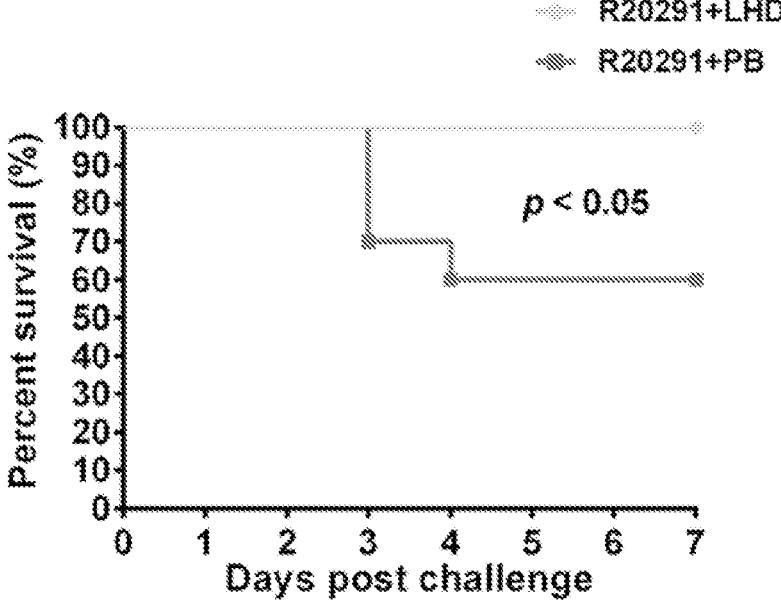
Figures 8A, 8B, 8C:
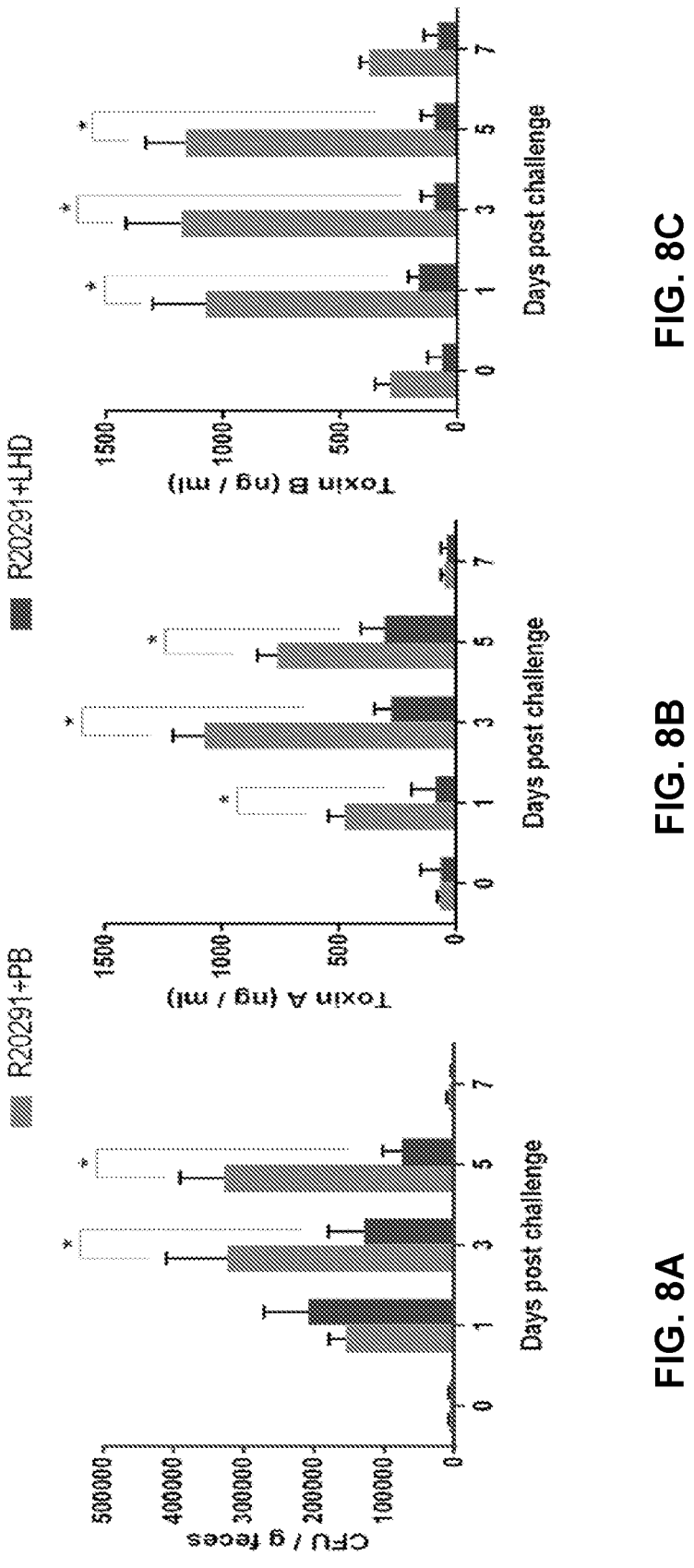
FIGS. 8A-8C show graphs that can demonstrate *C. difficile* spores and toxin levels in fecal samples of mice infected with *C. difficile* R20191 spores with/without LHD treatment. *C. difficile* spore numbers (FIG. 8A), Tcd A level (FIG. 8B), and Tcd B level (FIG. 8C) in two groups of mice infected with R20291 spores with/without LHD treatment, respectively. Experiments were repeated 3 times, and representative data were shown. Data are present as "Mean±SD". * p<0.05.
Figure 9:
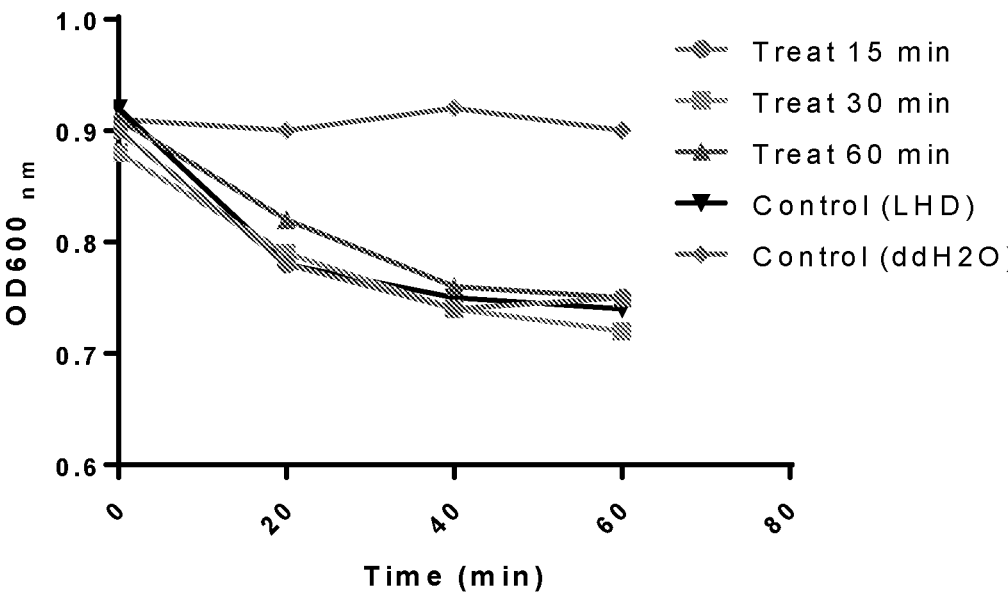
FIG. 9 shows a graph that can demonstrate the lytic activity of protein LHD on *C. difficile* R20291 after treatment in mouse intestinal contents. Protein LHD was incubated with mouse intestinal contents at 37° C. for 15, 30 or 60 minutes, then optical drop assays were performed on *C. difficile* R20291 to test the lytic activity of LHD at a concentration of 100 µg/ml. Experiments were repeated 3 times, and representative data were shown.

From the first day of post challenge, weight loss and diarrhea were observed among mice in both groups (FIGS. 7A-7C). However, treatment with LHD decreased both weight loss and diarrhea rate significantly (FIGS. 7A and 7B). The non-treatment group (R20291+PB) showed 90% diarrhea rate, and the diarrhea was observed during the 7-day experimental period (FIGS. 7B and 7C). While 60% of the mice treated with LHD displayed diarrhea, the symp- tom only lasted 3 days (FIGS. 7B and 7C). Death occurred in the non-treatment group (R20291+PB) from the 3rd day of post challenge, and only 60% of the mice finally survived (FIG. 7D). However, all mice receiving the treatment of LHD survived during the experimental period (FIG. 7D). In addition, treatment with LHD significantly decreased the number of *C. difficile* spores in feces (FIG. 8A), and also the toxin-level in feces (FIGS. 8B and 8C). To appreciate the stability and activity of LHD in the mouse intestine, LCD protein was incuated with freshly prepaerd mouse intestinal contents for different times, lytic activities of LHD treated with intestinal contents were determined on strain *C. difficile* R20291. As shown in FIG. 9, treatment with intestinal contents for 1 hr did not affect lytic activity of LHD.

Discussion

The prevalence and outbreak of CDI have caused serious morbidities and mortalities, and huge economical burdens worldwide (Napolitano and Edmiston 2017, Reigadas Ramirez and Bouza 2018). Studies on novel therapeutics such as the use of bacteriophages and their derivatives received increasing attentions. While phage therapy is pro- posed to be particularly suited for CDI treatment, the tech- nical difficulties of working with anaerobes limits the research in this area (Hargreaves and Clokie 2014). In this Example it can be demonstrated that the catalytic domain of the lysin from phage phiC2 (LCD) and its derivative (LHD) were potent against *C. difficile* in vitro and in vivo, indicat- ing the potential of phage lysins as therapeutics in the treatment of CDI.

This Example can also demonstrate that both LHD and LCD were potent against different types of *C. difficile* strains, including 027, 078, 087, 012, and ST201 strains (e.g. FIG. 3), which can support a broad lytic activity. These types of *C. difficile* strains are clinical epidemic strains circulating in different regions of world (Li, Liu et al. 2015, Shin, Chaves-Olarte et al. 2016). In addition, both LHD and LCD had a lower MIC than the therapy antibiotics metronidazole and vancomycin (Table 2). These findings suggest a good potential of at least the two proteins of this Example as therapeutics against CDI.

In addition to the catalytic domain of the lysin from phage phiC2, another part designed for the lysin-human defensin fusion protein is the functional domain of human alpha- defensin protein HD5 (FIGS. 1A-1B). This region inhibits hypervirulent *C. difficile* strains (Furci, Baldan et al. 2015). It was observed that the lysin-human defensin fusion protein LHD had a lower MIC on *C. difficile* R20291 than the lysin catalytic domain LCD (Table 2), indicating that the addition of the human alpha-defensin peptide may increase the lytic effect of the phage lysin catalytic domain.

It has been reported that TcdB is essential for virulence of *C. difficile* (Lyras, O'Connor et al. 2009). The human defensin protein HD5 has an inhibitory role on TcdB (Gie- semann, Guttenberg et al. 2008). This Example can demon- strate showed that the lysin-human defensin fusion protein LHD was comparable to human defensin peptide HD5 in inhibiting cell rounding caused by TcdB (FIG. 5A). Inhibi- tion of TcdB by LHD or HD was further confirmed by measuring the non-glucoslated Rac1 (FIGS. 5B-5C), which is one of the known intracellular RhoGTPase targets of *C. difficile* toxins (Just and Gerhard 2004).

The potential application of the lysin-human defensin fusion protein on combating CDI was also demonstrated by its treatment efficacy in mouse model of CDI (FIGS. 7A-7D). In this study, we delivered the protein LHD to the *C. difficile*-challenged mice by gavage. Even though the presence of stomach acid might influence the efficacy of LHD on *C. difficile*, however, in the animal experiment, mice were continuously gavaged twice a day for 7 days at 400 μg LHD in 200 μl of PBS per dose. This large volume of PBS may neutralize the stomach acid, protecting LHD there. In addition, as an alkaline protein (P1=9.10), LHD may also neutralize the stomach acid, and stay effective against *C. difficile* in the gut. The weight recovery of the mice receiving LHD was slower than those given PBS at the late stage of the tests (from 3 dpi to 7 dpi, FIG. 7A), which might be caused by the administration of LHD (twice a day), limiting the food intake of mice.

In sum, this Example describes, interalia, an engineered lysin-human defensin fusion protein based on the phage lysin protein and human alpha-defensin 5 peptide. Both in vitro and in vivo tests suggest this engineered lysin-human defensin fusion protein can be effective to help treat CDI.

REFERENCES

Aktories, K., C. Schwan and T. Jank (2017). "*Clostridium difficile* Toxin Biology." Annu Rev Microbiol 71: 281-307.

Cassini, A., D. Plachouras, T. Eckmanns, M. Abu Sin, H. P. Blank, T. Ducomble, S. Haller, T. Harder, A. Klingeberg, M. Sixtensson, E. Velasco, B. Weiss, P. Kramarz, D. L. Monnet, M. E. Kretzschmar and C. Suetens (2016). "Burden of Six Healthcare-Associated Infections on European Population Health: Estimating Incidence-Based Disability-Adjusted Life Years through a Population Prevalence-Based Modelling Study." PLoS Med 13(10): e1002150.

CDC (2013). "Antibiotic Resistance Threats in the United States, 2013."

Debast, S. B., M. P. Bauer and E. J. Kuijper (2014). "European Society of Clinical Microbiology and Infectious Diseases: update of the treatment guidance document for *Clostridium difficile* infection." Clin Microbiol Infect 20 Suppl 2: 1-26.

Finney, J. M. (1893). "Gastro-enterostomy for cicatrizing ulcer of the pylorus." Bull Johns Hopkins Hospital 4: 53.

Furci, L., R. Baldan, V. Bianchini, A. Trovato, C. Ossi, P. Cichero and D. M. Cirillo (2015). "New role for human alpha-defensin 5 in the fight against hypervirulent *Clostridium difficile* strains." Infect Immun 83(3): 986-995.

Giesemann, T., G. Guttenberg and K. Aktories (2008). "Human alpha-defensins inhibit *Clostridium difficile* toxin B." Gastroenterology 134(7): 2049-2058.

Gilmer, D. B., J. E. Schmitz, M. Thandar, C. W. Euler and V. A. Fischetti (2017). "The Phage Lysin PlySs2 Decolonizes *Streptococcus suis* from Murine Intranasal Mucosa." PLoS One 12(1): e0169180.

Hargreaves, K. R. and M. R. Clokie (2014). "*Clostridium difficile* phages: still difficult?" Front Microbiol 5: 184.

Just, I. and R. Gerhard (2004). "Large clostridial cytotoxins." Rev Physiol Biochem Pharmacol 152: 23-47.

Lawson, P. A., D. M. Citron, K. L. Tyrrell and S. M. Finegold (2016). "Reclassification of *Clostridium difficile* as *Clostridioides difficile* (Hall and O'Toole 1935) Prevot 1938." Anaerobe 40: 95-99.

Li, C., S. Liu, P. Zhou, J. Duan, Q. Dou, R. Zhang, H. Chen, Y. Cheng and A. Wu (2015). "Emergence of a Novel Binary Toxin-Positive Strain of *Clostridium difficile* Associated With Severe Diarrhea That Was Not Ribotype 027 and 078 in China." Infect Control Hosp Epidemiol 36(9): 1112-1114.

Lyras, D., J. R. O'Connor, P. M. Howarth, S. P. Sambol, G. P. Carter, T. Phumoonna, R. Poon, V. Adams, G. Vedantam, S. Johnson, D. N. Gerding and J. I. Rood (2009). "Toxin B is essential for virulence of *Clostridium difficile*." Nature 458(7242): 1176-1179.

McDonald, L. C., D. N. Gerding, S. Johnson, J. S. Bakken, K. C. Carroll, S. E. Coffin, E. R. Dubberke, K. W. Garey, C. V. Gould, C. Kelly, V. Loo, J. Shaklee Sammons, T. J. Sandora and M. H. Wilcox (2018). "Clinical Practice Guidelines for *Clostridium difficile* Infection in Adults and Children: 2017 Update by the Infectious Diseases Society of America (IDSA) and Society for Healthcare Epidemiology of America (SHEA)." Clin Infect Dis 66(7): 987-994.

Napolitano, L. M. and C. E. Edmiston, Jr. (2017). "*Clostridium difficile* disease: Diagnosis, pathogenesis, and treatment update." Surgery 162(2): 325-348.

Peng, Z., A. Addisu, S. Alrabaa and X. Sun (2017). "Antibiotic Resistance and Toxin Production of *Clostridium difficile* Isolates from the Hospitalized Patients in a Large Hospital in Florida." Front Microbiol 8: 2584.

Peng, Z., D. Jin, H. B. Kim, C. W. Stratton, B. Wu, Y. W. Tang and X. Sun (2017). "Update on Antimicrobial Resistance in *Clostridium difficile*: Resistance Mechanisms and Antimicrobial Susceptibility Testing." J Clin Microbiol 55(7): 1998-2008.

Peng, Z., S. Liu, X. Meng, W. Liang, Z. Xu, B. Tang, Y. Wang, J. Duan, C. Fu, B. Wu, A. Wu and C. Li (2017). "Genome characterization of a novel binary toxin-positive strain of *Clostridium difficile* and comparison with the epidemic 027 and 078 strains." Gut Pathog 9: 42.

Reigadas Ramirez, E. and E. S. Bouza (2018). "Economic Burden of *Clostridium difficile* Infection in European Countries." Adv Exp Med Biol 1050: 1-12.

Roy Chowdhury, P., M. DeMaere, T. Chapman, P. Worden, I. G. Charles, A. E. Darling and S. P. Djordjevic (2016). "Comparative genomic analysis of toxin-negative strains of *Clostridium difficile* from humans and animals with symptoms of gastrointestinal disease." BMC Microbiol 16: 41.

Shin, J. H., E. Chaves-Olarte and C. A. Warren (2016). "*Clostridium difficile* Infection." Microbiol Spectr 4(3).

Spigaglia, P. (2016). "Recent advances in the understanding of antibiotic resistance in *Clostridium difficile* infection." TherAdv Infect Dis 3(1): 23-42.

Wang, Q., C. W. Euler, A. Delaune and V. A. Fischetti (2015). "Using a Novel Lysin To Help Control *Clostridium difficile* Infections." Antimicrob Agents Chemother 59(12): 7447-7457.

Wiegand, I., K. Hilpert and R. E. Hancock (2008). "Agar and broth dilution methods to determine the minimal inhibitory concentration (MIC) of antimicrobial substances." Nat Protoc 3(2): 163-175.

Zhang, K., S. Zhao, Y. Wang, X. Zhu, H. Shen, Y. Chen and X. Sun (2015). "The non-toxigenic *Clostridium difficile* CD37 protects mice against infection with a BI/NAP1/027 type of *C. difficile* strain." Anaerobe 36: 49-52.

Zhang, Y., L. Shi, S. Li, Z. Yang, C. Standley, Z. Yang, R. ZhuGe, T. Savidge, X. Wang and H. Feng (2013). "A segment of 97 amino acids within the translocation domain of *Clostridium difficile* toxin B is essential for toxicity." PLoS One 8(3): e58634.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant lysin-human defensin (LHD) protein comprising a catalytic domain of a lysin protein of *C. difficile* phage phiC2 comprising the amino acid sequence of SEQ ID NO:2, wherein the lysin protein is operatively coupled via a linker comprising the amino acid sequence of SEQ ID NO:4 (GGGGS)$_3$ to a human alpha-defensin 5 polypeptide comprising the amino acid sequence of SEQ ID NO: 3, wherein the recombinant lysin-human defensin protein is capable of specifically lysing *Clostridium difficile*.

2. The recombinant LHD protein of claim 1, wherein the recombinant LHD protein is capable of inhibiting one or more *Clostridium difficile* toxins.

3. A pharmaceutical formulation comprising:

an amount of the recombinant lysin-human defensin (LHD) protein as in claim 1; and a pharmaceutically acceptable carrier.

4. The pharmaceutical formulation of claim 3, wherein the amount of the recombinant LHD protein is a therapeutically effective amount.

5. A DNA molecule encoding the recombinant lysin-human defensin (LHD) protein of claim 1.

6. A vector comprising the DNA molecule of claim 5.

7. A cell comprising the vector of claim 6.

8. The cell of claim 7, wherein the cell is a prokaryotic cell.

9. The cell of claim 7, wherein the cell is a eukaryotic cell.

10. A method comprising:

administering the recombinant lysin-human defensin (LHD) protein of claim 1 or a pharmaceutical formulation thereof to a subject.

11. The method of claim 10, wherein the subject has or is suspected of having a *Clostridium difficile* infection.

12. A method of treating *Clostridium difficile* or a symptom thereof in subject in need thereof, the method comprising:

administering the recombinant lysin-human defensin (LHD) protein of claim 1 or a pharmaceutical formulation thereof to the subject in need thereof.

13. A kit comprising:

an amount of the recombinant lysin-human defensin (LHD) protein of claim 1 or a pharmaceutical formulation thereof; and instructions fixed in a tangible medium of expression that comprise directions for administering the LHD protein or pharmaceutical formulation thereof to a subject having or suspected of having a *Clostridium difficile* infection.

\* \* \* \* \*